US010286905B2

(12) United States Patent
Lee

(10) Patent No.: US 10,286,905 B2
(45) Date of Patent: May 14, 2019

(54) DRIVER ASSISTANCE APPARATUS AND CONTROL METHOD FOR THE SAME

(71) Applicant: LG ELECTRONICS INC., Seoul (KR)

(72) Inventor: Choil Lee, Seoul (KR)

(73) Assignee: LG Electronics Inc., Seoul (KR)

( * ) Notice: Subject to any disclaimer, the term of this patent is extended or adjusted under 35 U.S.C. 154(b) by 73 days.

(21) Appl. No.: 15/225,985

(22) Filed: Aug. 2, 2016

(65) Prior Publication Data
US 2017/0036673 A1 Feb. 9, 2017

(30) Foreign Application Priority Data
Aug. 3, 2015 (KR) .................. 10-2015-0109599

(51) Int. Cl.
| | | |
|---|---|---|
| *A61B 3/11* | (2006.01) | |
| *G05D 1/02* | (2006.01) | |
| *A61B 5/024* | (2006.01) | |
| *B60W 30/09* | (2012.01) | |
| *G06K 9/00* | (2006.01) | |
| *A61B 5/16* | (2006.01) | |

(Continued)

(52) U.S. Cl.
CPC ............ *B60W 30/09* (2013.01); *A61B 3/112* (2013.01); *A61B 5/024* (2013.01); *A61B 5/165* (2013.01);
(Continued)

(58) Field of Classification Search
CPC .... G08G 1/166; G05D 1/0246; G05D 1/0223; G06F 3/14; G06F 3/017; B60W 30/09;
(Continued)

(56) References Cited

U.S. PATENT DOCUMENTS

| | | | | |
|---|---|---|---|---|
| 4,802,437 A | * | 2/1989 | Felicetti | .................... G01P 1/08 |
| | | | | 116/62.1 |
| 5,521,580 A | * | 5/1996 | Kaneko | .................. B60K 28/02 |
| | | | | 180/272 |

(Continued)

FOREIGN PATENT DOCUMENTS

| | | |
|---|---|---|
| JP | 2003-200782 | 7/2003 |
| JP | 2006-085285 | 3/2006 |

(Continued)

OTHER PUBLICATIONS

Partial European Search Report in European Application No. 16181941.2, dated Jan. 16, 2017, 7 pages (with English translation).

*Primary Examiner* — Behrang Badhii
*Assistant Examiner* — Daniel L Greene
(74) *Attorney, Agent, or Firm* — Fish & Richardson P.C.

(57) ABSTRACT

Disclosed are driver assistance apparatus and a control method for the same. The driver assistance apparatus includes a sensing unit configured to acquire information regarding an object outside a vehicle, the object including a first other vehicle being driven in the vicinity of the vehicle, and a processor configured to judge whether the first other vehicle is a dangerous vehicle based on at least one of the information regarding the object, user input provided from a driver of the vehicle, information regarding the state of the driver, and information regarding the first other vehicle provided from a second other vehicle being driven in the vicinity of the vehicle, and to execute at least one predetermined operation upon judging that the first other vehicle is a dangerous vehicle.

18 Claims, 33 Drawing Sheets

(51) Int. Cl.
*A61B 5/18* (2006.01)
*B60W 30/095* (2012.01)
*B60W 30/182* (2012.01)
*B60W 50/12* (2012.01)
*G06F 3/01* (2006.01)
*G06F 3/14* (2006.01)
*G08G 1/16* (2006.01)
*B60W 50/14* (2012.01)

(52) U.S. Cl.
CPC ........... *A61B 5/18* (2013.01); *B60W 30/0956* (2013.01); *B60W 30/182* (2013.01); *B60W 50/12* (2013.01); *G05D 1/0223* (2013.01); *G05D 1/0246* (2013.01); *G06F 3/017* (2013.01); *G06F 3/14* (2013.01); *G06K 9/00805* (2013.01); *G06K 9/00845* (2013.01); *G08G 1/166* (2013.01); *B60W 2050/146* (2013.01); *B60W 2420/42* (2013.01); *B60W 2520/06* (2013.01); *B60W 2520/105* (2013.01); *B60W 2520/125* (2013.01); *B60W 2540/22* (2013.01); *B60W 2600/00* (2013.01)

(58) Field of Classification Search
CPC ........... B60W 50/12; B60W 2050/146; B60W 30/182; B60W 30/0956; A61B 5/024; A61B 3/112; A61B 5/18; A61B 5/165
See application file for complete search history.

(56) References Cited

U.S. PATENT DOCUMENTS

| | | | | |
|---|---|---|---|---|
| 6,636,149 B2* | 10/2003 | Moon | ................... | G08G 1/163 340/435 |
| 6,721,659 B2* | 4/2004 | Stopczynski | ........ | B60R 21/013 180/274 |
| 2003/0220722 A1* | 11/2003 | Toba | ...................... | G10K 15/02 701/1 |
| 2005/0088318 A1* | 4/2005 | Liu | ...................... | G08G 1/0965 340/902 |
| 2006/0167605 A1* | 7/2006 | Darvish | .............. | B60R 21/0132 701/45 |
| 2008/0055068 A1* | 3/2008 | Van Wageningen | ........................ | H04W 52/10 340/539.3 |
| 2009/0292459 A1* | 11/2009 | Zuccotti | ........... | G08G 1/096716 701/532 |
| 2012/0173069 A1* | 7/2012 | Tsimhoni | .............. | G01C 21/365 701/25 |
| 2013/0090843 A1* | 4/2013 | Funabashi | ........... | G08G 1/0969 701/300 |
| 2015/0116493 A1* | 4/2015 | Bala | ................... | G06K 9/00845 348/148 |
| 2015/0328985 A1* | 11/2015 | Kim | ................... | H04N 5/23229 180/272 |

FOREIGN PATENT DOCUMENTS

| | | | |
|---|---|---|---|
| JP | 2006085285 A | * | 3/2006 |
| JP | 2007080060 A | * | 3/2007 |
| JP | 20070080060 | | 3/2007 |
| JP | 2009-037561 | | 2/2009 |
| JP | 2014-075008 | | 4/2014 |
| KR | 10-0934942 | | 1/2010 |
| KR | 10-2010-0043875 | | 4/2010 |
| KR | 10-2013-0058991 | | 6/2013 |
| KR | 10-2015-0043663 | | 4/2015 |
| KR | 10-2015-0087737 | | 7/2015 |

* cited by examiner

FIG. 15C
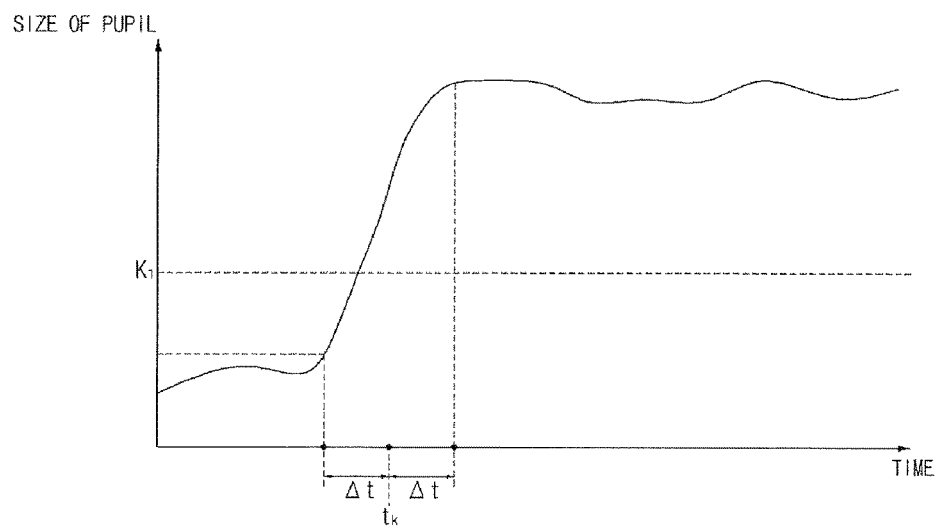
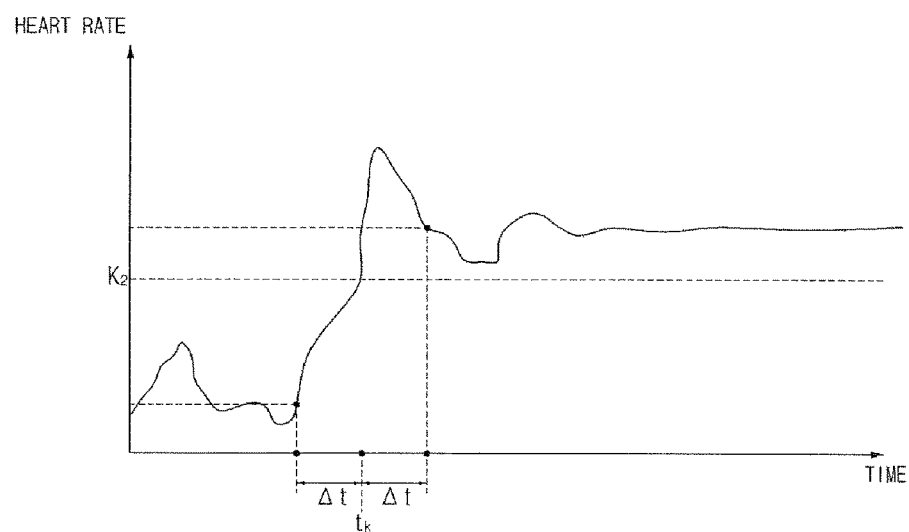

DRIVER ASSISTANCE APPARATUS AND CONTROL METHOD FOR THE SAME

CROSS-REFERENCE TO RELATED APPLICATION

This application claims the priority benefit of Korean Patent Application No. 10-2015-0109599, filed on, Aug. 3, 2015 in the Korean Intellectual Property Office, the disclosure of which is incorporated herein by reference.

BACKGROUND OF THE INVENTION

1. Field of the Invention

The present invention relates to a driver assistance apparatus and an operating method for the same and, more particularly, to a driver assistance apparatus which executes an operation in response to the movement of another vehicle, and an operating method for the same.

2. Description of the Related Art

A vehicle is an apparatus that transports, for example, people or cargo from one place to another place via driving of wheels. Examples of vehicles include two-wheeled cars such as motorcycles, four-wheeled cars such as sedans, and trains.

In recent years, in order to increase the safety and convenience of a user who uses the vehicle, technology to equip vehicles with, for example, a variety of sensors and electronic devices is being aggressively developed. In particular, for example, various types of driver assistance apparatuses, which are developed for user driving convenience, have been mounted in vehicles.

When another vehicle in the vicinity of a vehicle is being driven abnormally or dangerously, for example, repeatedly and abruptly decelerates or brakes, or suddenly has cut in front of the vehicle, there is a high likelihood that the vehicle will collide with the other vehicle. In addition, the driver has difficulty in judging how to operate the vehicle in order to avoid the other vehicle.

In another frequently occurring scenario in which another vehicle, which is being driven dangerously in the vicinity of a corresponding vehicle, is hidden by objects near the road or by other vehicles, the anxiety of the driver of the corresponding vehicle may increase because the other vehicle that is being dangerously driven is not in the visual field of the driver who sitting in the corresponding vehicle.

SUMMARY OF THE INVENTION

Therefore, the present invention is made to solve the problems as described above and one object of the present invention is to provide a driver assistance apparatus, which is capable of judging, based on the movement of at least one other vehicle in the vicinity of a vehicle, whether the other vehicle is a dangerous vehicle, and a control method for the same.

In addition, another object of the present invention is to provide a driver assistance apparatus, which is capable of automatically controlling at least one of the steering, speed reduction, and acceleration of a vehicle based on a driving pattern of another vehicle that is being driven dangerously, and a control method for the same.

In addition, a further object of the present invention is to provide a driver assistance apparatus, which is capable of externally providing information related to another vehicle being driven dangerously, and a control method for the same.

Objects of the present invention should not be limited to the aforementioned object and other not-mentioned objects will be clearly understood by those skilled in the art from the following description.

In accordance with an aspect of the present invention, the above and other objects can be accomplished by the provision of a driver assistance apparatus including a sensing unit configured to acquire information regarding an object outside a vehicle, the object including a first other vehicle being driven in the vicinity of the vehicle, and a processor configured to judge whether the first other vehicle is a dangerous vehicle based on at least one of the information regarding the object, user input provided from a driver of the vehicle, the state of the driver, and information regarding the first other vehicle provided from a second other vehicle being driven in the vicinity of the vehicle, and to execute at least one predetermined operation upon judging that the first other vehicle is a dangerous vehicle.

Detailed items of other embodiments are included in the following description and the accompanying drawings.

BRIEF DESCRIPTION OF THE DRAWINGS

The above and other objects, features and advantages of the present invention will be more clearly understood from the following detailed description taken in conjunction with the accompanying drawings, in which:

FIGS. 15A to 15C are views respectively illustrating the situation in which the driver assistance apparatus according to one embodiment of the present invention determines any dangerous vehicle in the vicinity of a vehicle;

DETAILED DESCRIPTION OF THE PREFERRED EMBODIMENTS

Figure 1:
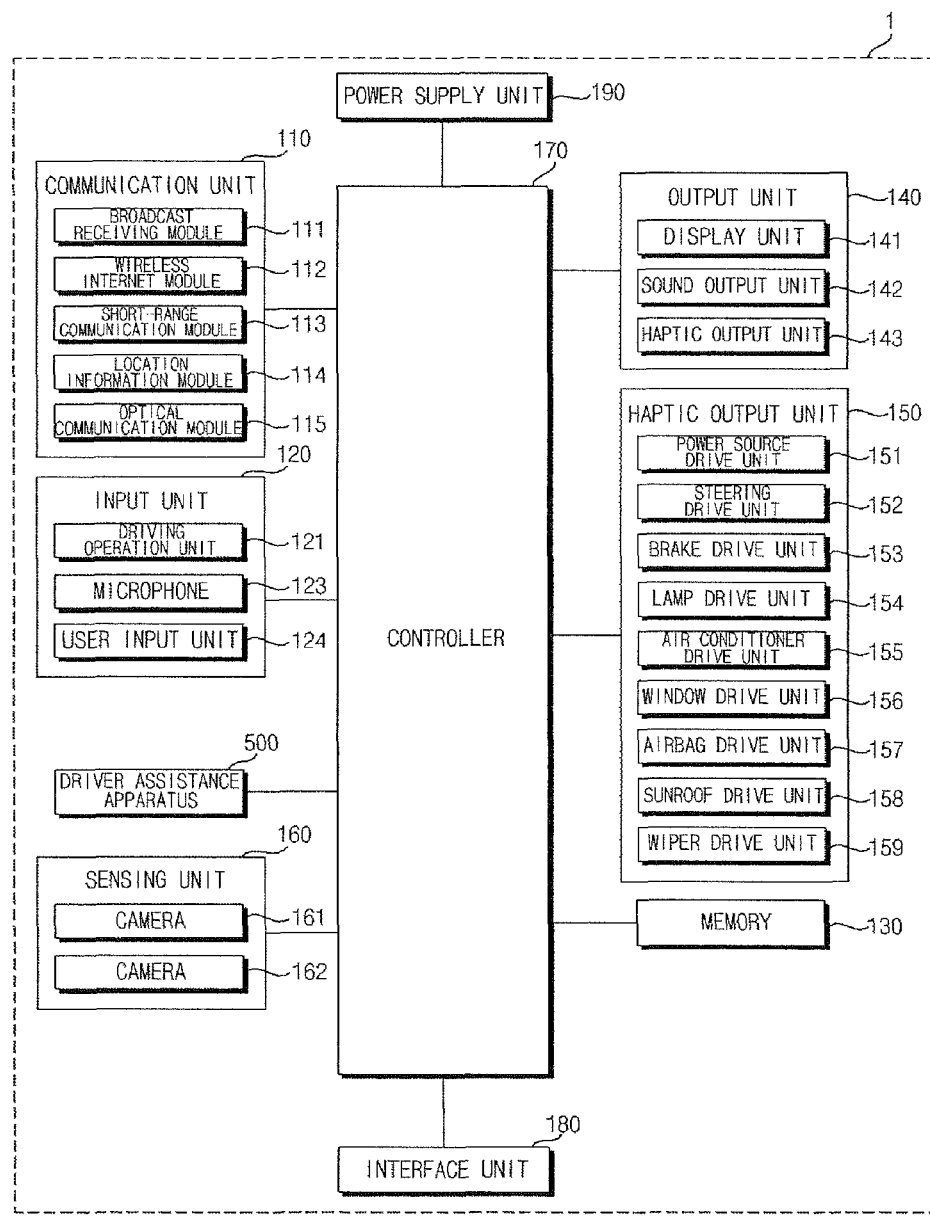
FIG. 1 is a block diagram of a vehicle according to one embodiment of the present invention.

Hereinafter, the embodiments disclosed in the present specification will be described in detail with reference to the accompanying drawings, and the same or similar elements are denoted by the same reference numerals even though they are depicted in different drawings and redundant descriptions thereof will be omitted. In the following description, with respect to constituent elements used in the following description, suffixes "module" and "unit" are given or mingled with each other only in consideration of ease in the preparation of the specification, and do not have or serve as different meanings. Accordingly, the suffixes "module" and "unit" may be mingled with each other. In addition, in the following description of the embodiments disclosed in the present specification, a detailed description of known functions and configurations incorporated herein will be omitted when it may make the subject matter of the embodiments disclosed in the present specification rather unclear. In addition, the accompanying drawings are provided only for a better understanding of the embodiments disclosed in the present specification and are not intended to limit technical ideas disclosed in the present specification. Therefore, it should be understood that the accompanying drawings include all modifications, equivalents and substitutions included in the scope and sprit of the present invention.

It will be understood that although the terms first, second, etc., may be used herein to describe various components, these components should not be limited by these terms. These terms are only used to distinguish one component from another component.

It will be understood that when a component is referred to as being "connected to" or "coupled to" another component, it may be directly connected to or coupled to another component or intervening components may be present. In contrast, when a component is referred to as being "directly connected to" or "directly coupled to" another component, there are no intervening components present. In addition, it will be understood that when a component is referred to as "controlling" another component, it may directly control another component, or may also control another component via the mediation of a third component. In addition, it will be understood that when a component is referred to as "providing" another component with information and signals, it may directly provide another component with the same and may also provide another component the same via the mediation of a third component.

As used herein, the singular form is intended to include the plural forms as well, unless the context clearly indicates otherwise.

In the present application, it will be further understood that the terms "comprises", includes," etc. specify the presence of stated features, integers, steps, operations, elements, components, or combinations thereof, but do not preclude the presence or addition of one or more other features, integers, steps, operations, elements, components, or combinations thereof.

A vehicle as described in this specification may include all of an internal combustion engine vehicle including an engine as a power source, a hybrid vehicle including both an engine and an electric motor as a power source, and an electric vehicle including an electric motor as a power source.

FIG. 1 is a block diagram of a vehicle 1 according to one embodiment of the present invention.

The vehicle 1 may include a communication unit 110, an input unit 120, a memory 130, an output unit 140, a vehicle drive unit 150, a sensing unit 160, a controller 170, an interface unit 180, a power supply unit 190, and a driver assistance apparatus 500.

The communication unit 110 may include one or more modules to enable the wireless communication between the vehicle 1 and an external appliance (e.g., a mobile terminal, an external server, or another vehicle). In addition, the communication unit 110 may include one or more modules to connect the vehicle 1 to one or more networks.

The communication unit 110 may include a broadcast receiving module 111, a wireless Internet module 112, a short-range communication module 113, a location information module 114, and an optical communication module 115.

The broadcast receiving module 111 is configured to receive a broadcast signal or broadcast associated information from an external broadcast managing server via a broadcast channel. Here, broadcast includes radio broadcast or TV broadcast.

The wireless Internet module 112 is a module for wireless Internet access. The wireless Internet module 112 may be internally or externally coupled to the vehicle 1. The wireless Internet module 712 is configured to transmit or receive wireless signals via communication networks according to wireless Internet technologies.

Examples of such wireless Internet technologies include Wireless LAN (WLAN), Wireless Fidelity (Wi-Fi), Wi-Fi Direct, Digital Living Network Alliance (DLNA), Wireless Broadband (WiBro), Worldwide Interoperability for Microwave Access (WiMAX), High Speed Downlink Packet Access (HSDPA), High Speed Uplink Packet Access (HSUPA), Long Term Evolution (LTE), and LTE-A (Long Term Evolution-Advanced). The wireless Internet module 112 transmits and receives data according to one or more of such wireless Internet technologies and other Internet technologies as well. For example, the wireless Internet module 112 may exchange data with the external server in a wireless manner. The wireless Internet module 112 may receive weather information and road traffic state information (e.g., Transport Protocol Expert Group (TPEG) information) from the external server.

The short-range communication module 113 may assist short-range communication using at least one selected from among Bluetooth™, Radio Frequency IDdentification (RFID), Infrared Data Association (IrDA), Ultra-WideBand (UWB), ZigBee, Near Field Communication (NFC), Wireless-Fidelity (Wi-Fi), Wi-Fi Direct, Wireless USB (Wireless Universal Serial Bus), and the like.

The short-range communication module 113 may form wireless area networks to perform the short-range communication between the vehicle 1 and at least one external device. For example, the short-range communication module 113 may exchange data with a mobile terminal of a passenger in a wireless manner. The short-range communication module 113 may receive weather information and road traffic state information (e.g., Transport Protocol Expert Group (TPEG) information) from the mobile terminal or the external server. When a user gets into the vehicle 1, the mobile terminal of the user and the vehicle 1 may pair with each other automatically or as the user executes a pairing application.

The location information module 114 is a module to acquire a location of the vehicle 1. A representative example of the location information module 114 includes a Global Position System (GPS) module. For example, when the vehicle utilizes a GPS module, a location of the vehicle 1 may be acquired using signals transmitted from GPS satellites.

The optical communication module 115 may include a light emitting unit and a light receiving unit.

The light receiving unit may convert light into electrical signals to receive information. The light receiving unit may include Photo Diodes (PDPs) to receive light. The photo diodes may convert light into electrical signals. For example, the light receiving unit may receive information regarding a preceding vehicle via light emitted from a light source included in the preceding vehicle.

The light emitting unit may include at least one light emitting element to convert electrical signals into light. Here, the light emitting element may be a Light Emitting Diode (LED). The light emitting unit converts electrical signals into light to thereby emit the light. For example, the light emitting unit may externally emit light via flickering of the light emitting element corresponding to a prescribed frequency. In some embodiments, the light emitting unit may include an array of a plurality of light emitting elements. In some embodiments, the light emitting unit may be integrated with a lamp provided in the vehicle 1. For example, the light emitting unit may be at least one selected from among a headlight, a taillight, a brake light, a turn signal light, and a sidelight. For example, the optical communication module 115 may exchange data with another vehicle via optical communication.

The input unit 120 may include a driving operation unit 121, a microphone 123, and a user input unit 124.

The driving operation unit 121 is configured to receive user input for the driving of the vehicle 1. The driving operation unit 121 may include a steering input unit 121a, a shift input unit 121b, an acceleration input unit 121c, and a brake input unit 121d.

The steering input unit 121a is configured to receive user input with regard to the direction of travel of the vehicle 1. The steering input unit 121a may include a steering wheel. In some embodiments, the steering input unit 121a may be configured as a touchscreen, a touch pad, or a button.

The shift input unit 121b is configured to receive input for selecting one of Park (P), Drive (D), Neutral (N), and Reverse (R) gears of the vehicle 1 from the user. The shift input unit 121b may have a lever form. In some embodiments, the shift input unit 121b may be configured as a touchscreen, a touch pad, or a button.

The acceleration input unit 121c is configured to receive user input for the acceleration of the vehicle 1. The brake input unit 121d is configured to receive user input for the speed reduction of the vehicle 1. Each of the acceleration input unit 121c and the brake input unit 121d may have a pedal form. In some embodiments, the acceleration input unit 121c or the brake input unit 121d may be configured as a touchscreen, a touch pad, or a button.

The microphone 123 may process external sound signals into electrical data. The processed data may be utilized in various ways according to a function that the vehicle 1 is performing. The microphone 123 may convert a user voice command into electrical data. The converted electrical data may be transmitted to the controller 170.

Meanwhile, in some embodiments, a camera 122 or the microphone 123 may be components of the sensing unit 160, other than components of the input unit 120.

The user input unit 124 is configured to receive information from the user. When information is input via the user input unit 124, the controller 170 may control the operation of the vehicle 1 to correspond to the input information. The user input unit 124 may include a touch input unit or a mechanical input unit. In some embodiments, the user input unit 124 may be located in a region of the steering wheel. In this case, the driver may operate the user input unit 124 with the fingers while gripping the steering wheel.

The sensing unit 160 is configured to sense signals associated with, for example, the driving of the vehicle 1. To this end, the sensing unit 160 may include a collision sensor, a steering sensor, a speed sensor, gradient sensor, a weight sensor, a heading sensor, a yaw sensor, a gyro sensor, a position module, a vehicle forward/reverse sensor, a battery sensor, a fuel sensor, a tire sensor, a steering sensor based on the rotation of the steering wheel, a vehicle interior temperature sensor, a vehicle interior humidity sensor, an ultrasonic sensor, an infrared sensor, a radar, and Lidar.

As such, the sensing unit 160 may acquire sensing signals with regard to, for example, vehicle collision information, vehicle traveling direction information, vehicle location information (GPS information), vehicle angle information, vehicle speed information, vehicle acceleration information, vehicle tilt information, vehicle forward/reverse information, battery information, fuel information, tire information, vehicle lamp information, vehicle interior temperature information, vehicle interior humidity information, and steering wheel rotation angle information. In addition, the driver assistance apparatus 500, which will be described below, may generate control signals for acceleration, speed reduction, direction change of the vehicle 1, for example, based on surrounding environment information acquired by at least one of the camera, the ultrasonic sensor, the infrared sensor, the radar, and Lidar included in the vehicle 1. Here, the surrounding environment information may be information related to various objects located within a prescribed distance range from the vehicle 1 that is traveling. For example, the surrounding environment information may include the number of obstacles located within a distance of 100 m from the vehicle 1, the distances to the obstacles, the sizes of the obstacles, the kinds of the obstacles, and the like.

Meanwhile, the sensing unit 160 may further include, for example, an accelerator pedal sensor, a pressure sensor, an engine speed sensor, an Air Flow-rate Sensor (AFS), an Air Temperature Sensor (ATS), a Water Temperature Sensor (WTS), a Throttle Position Sensor (TPS), a Top Dead Center (TDC) sensor, and a Crank Angle Sensor (CAS).

The sensing unit 160 may include a biometric information sensing unit. The biometric information sensing unit is configured to sense and acquire biometric information of the passenger. The biometric information may include fingerprint information, iris-scan information, retina-scan information, hand geometry information, facial recognition information, and voice recognition information. The biometric information sensing unit may include a sensor to sense biometric information of the passenger. Here, an internal camera 162 and the microphone 123 may operate as sensors. The biometric information sensing unit may acquire hand geometry information and facial recognition information via the internal camera 162.

The sensing unit 160 may include at least one camera 161 to capture an image of the outside of the vehicle 1. For example, the sensing unit 160 may include a plurality of cameras 161 arranged at different positions at the exterior of the vehicle 1. Each camera 161 may include an image sensor and an image processing module. The camera 161 may process a still image or moving image acquired by the image sensor (e.g., a CMOS or CCD). The image processing module may extract required information by processing the still image or moving image acquired by the image sensor, and may transmit the extracted information to the controller 170.

The sensing unit 160 may include at least one camera 162 to capture an image of the space inside the vehicle 1. For example, the camera 162 may form an image including a passenger of the vehicle 1 and then provide the controller 170 with the image.

The cameras 161 and 162 may respectively include the image sensor (e.g., a CMOS or CCD) and the image processing module. In addition, the cameras 161 and 162 may process a still image or moving image acquired by the image sensor. The image processing module may process a still image or moving image acquired by the image sensor. In addition, the cameras 161 and 162 may acquire an image including at least one of traffic lights, traffic signs, pedestrians, other vehicles, and road surfaces.

Meanwhile, although FIG. 1 illustrates the sensing unit 160 as being included in the vehicle 1, at least one sensor included in the sensing unit 160 may be described as a component included in the driver assistance apparatus 500 rather than the vehicle 1.

The output unit 140 is configured to output information processed in the controller 170. The output unit 140 may include a display unit 141, a sound output unit 142, and a haptic output unit 143.

The display unit 141 may display information processed in the controller 170. For example, the display unit 141 may display vehicle associated information. Here, the vehicle associated information may include vehicle control information for the direct control of the vehicle 1 or driver assistance information to guide the driver's vehicle driving. In addition, the vehicle associated information may include vehicle state information that indicates the current state of the vehicle or vehicle traveling information regarding the traveling of the vehicle.

The display unit 141 may include at least one selected from among a Liquid Crystal Display (LCD), a Thin Film Transistor LCD (TFT LCD), an Organic Light Emitting Diode (OLED), a flexible display, a 3D display, and an e-ink display.

The display unit 141 may configure an inter-layer structure with a touch sensor, or may be integrally formed with the touch sensor to implement a touchscreen. The touchscreen may function as the user input unit 124 which provides an input interface between the vehicle 1 and the user and also function to provide an output interface between the vehicle 1 and the user. In this case, the display unit 141 may include a touch sensor which senses a touch to the display unit 141 so as to receive a control command in a touch manner. When a touch is input to the display unit 141 as described above, the touch sensor may sense the touch and the controller 170 may generate a control command corresponding to the touch. Content input in a touch manner may be characters or numbers, or may be, for example, instructions in various modes or menu items that may be designated.

Meanwhile, the display unit 141 may include a cluster to allow the driver to check vehicle state information or vehicle traveling information while driving the vehicle. The cluster may be located on a dashboard. In this case, the driver may check information displayed on the cluster while looking forward.

Meanwhile, in some embodiments, the display unit 141 may be implemented as a Head Up display (HUD). When the display unit 141 is implemented as a HUD, information may be output via a transparent display provided at the windshield. Alternatively, the display unit 141 may include a projector module to output information via an image projected to the windshield.

The sound output unit 142 is configured to convert electrical signals from the controller 170 into audio signals and to output the audio signals. To this end, the sound output unit 142 may include, for example, a speaker. The sound output unit 142 may output sound corresponding to the operation of the user input unit 124.

The haptic output unit 143 is configured to generate tactile output. For example, the haptic output unit 143 may operate to vibrate a steering wheel, a safety belt, or a seat so as to allow the user to recognize an output thereof.

The vehicle drive unit 150 may control the operation of various devices of the vehicle 1. The vehicle drive unit 150 may include at least one of a power source drive unit 151, a steering drive unit 152, a brake drive unit 153, a lamp drive unit 154, an air conditioner drive unit 155, a window drive unit 156, an airbag drive unit 157, a sunroof drive unit 158, and a wiper drive unit 159.

The power source drive unit 151 may perform electronic control for a power source inside the vehicle 1. The power source drive unit 151 may include an acceleration device to increase the speed of the vehicle 1 and a speed reduction device to reduce the speed of the vehicle 1.

For example, in the case where a fossil fuel based engine (not illustrated) is a power source, the power source drive unit 151 may perform electronic control for the engine. As such, the power source drive unit 151 may control, for example, an output torque of the engine. In the case where the power source drive unit 151 is the engine, the power source drive unit 151 may control the speed of the vehicle by controlling the output torque of the engine under the control of the controller 170.

In another example, in the case where an electric motor (not illustrated) is a power source, the power source drive unit 151 may perform control for the motor. As such, the power source drive unit 151 may control, for example, the RPM and torque of the motor.

The steering drive unit 152 may include a steering apparatus. Thus, the steering drive unit 152 may perform electronic control for a steering apparatus inside the vehicle 1. For example, the steering drive unit 152 may include a steering torque sensor, a steering angle sensor, and a steering motor. The steering torque, applied to the steering wheel 12 by the driver, may be sensed by the steering torque sensor.

The steering drive unit 152 may control steering force and a steering angle by changing the magnitude and direction of current applied to the steering motor based on, for example, the speed and the steering torque of the vehicle 1. In addition, the steering drive unit 152 may judge whether the direction of travel of the vehicle 1 is correctly being adjusted based on steering angle information acquired by the steering angle sensor. As such, the steering drive unit 152 may change the direction of travel of the vehicle 1. In addition, the steering drive unit 152 may reduce the sense of weight of the steering wheel 12 by increasing the steering force of the steering motor when the vehicle 1 travels at a low speed and may increase the sense of weight of the steering wheel 12 by reducing the steering force of the steering motor when the vehicle 1 travels at a high speed. In addition, when the autonomous driving function of the vehicle 1 is executed, the steering drive unit 152 may control the steering motor to generate appropriate steering force based on, for example, the sensing signals output from the sensing unit 160 or control signals provided by a processor 570 even in the state in which the driver operates the steering wheel 12 (i.e. in the state in which no steering torque is sensed).

The brake drive unit 153 may perform electronic control of a brake apparatus (not illustrated) inside the vehicle 1. For example, the brake drive unit 153 may reduce the speed of the vehicle 1 by controlling the operation of brakes located at wheels. In another example, the brake drive unit 153 may adjust the direction of travel of the vehicle 1 leftward or rightward by differentiating the operation of respective brakes located at left and right wheels.

The lamp drive unit 154 may turn at least one lamp arranged inside and outside the vehicle 1 on or off. The lamp drive unit 154 may include a lighting apparatus. In addition, the lamp drive unit 154 may control, for example, the intensity and direction of light of each lamp included in the lighting apparatus. For example, the lamp drive unit 154 may perform control for a turn signal lamp, a headlamp or a brake lamp.

The air conditioner drive unit 155 may perform the electronic control of an air conditioner (not illustrated) inside the vehicle 1. For example, when the interior temperature of the vehicle 1 is high, the air conditioner drive unit 155 may operate the air conditioner to supply cold air to the interior of the vehicle 1.

The window drive unit 156 may perform the electronic control of a window apparatus inside the vehicle 1. For example, the window drive unit 156 may control the opening or closing of left and right windows of the vehicle 1.

The airbag drive unit 157 may perform the electronic control of an airbag apparatus inside the vehicle 1. For example, the airbag drive unit 157 may control an airbag to be deployed in a dangerous situation.

The sunroof drive unit 158 may perform electronic control of a sunroof apparatus (not illustrated) inside the vehicle 1. For example, the sunroof drive unit 158 may control the opening or closing of a sunroof.

The wiper drive unit 159 may perform the control of wipers 14a and 14b included in the vehicle 1. For example, the wiper drive unit 159 may perform electronic control with regard to, for example, the number of operations and the speed of operation of the wipers 14a and 14b in response to user input upon receiving the user input that directs operation of the wipers 14a and 14b through the user input unit 124. In another example, the wiper drive unit 159 may judge the amount or strength of rainwater based on sensing signals of a rain sensor included in the sensing unit 160 so as to automatically operate the wipers 14a and 14b without the user input.

Meanwhile, the vehicle drive unit 150 may further include a suspension drive unit (not illustrated). The suspension drive unit may perform the electronic control of a suspension apparatus (not illustrated) inside the vehicle 1. For example, in the case where the road surface is uneven, the suspension drive unit may control the suspension apparatus to reduce vibration of the vehicle 1.

The memory 130 is electrically connected to the controller 170. The memory 130 may store basic data for each unit, control data for the operation control of the unit, and input/output data. The memory 130 may be any of various storage devices such as, for example, a ROM, a RAM, an EPROM, a flash drive, and a hard drive. The memory 130 may store various data for the overall operation of the vehicle 1 such as, for example, programs for the processing or control of the controller 170.

The interface unit 180 may serve as a passage for various kinds of external devices that are connected to the vehicle 1. For example, the interface unit 180 may have a port that is connectable to a mobile terminal and may be connected to the mobile terminal via the port. In this case, the interface unit 180 may exchange data with the mobile terminal.

The controller 170 may control the overall operation of each unit inside the vehicle 1. The controller 170 may be referred to as an Electronic Control Unit (ECU).

The controller 170 may be implemented in a hardware manner using at least one selected from among Application Specific Integrated Circuits (ASICs), Digital Signal Processors (DSPs), Digital Signal Processing Devices (DSPDs), Programmable Logic Devices (PLDs), Field Programmable Gate Arrays (FPGAs), processors, controllers, micro-controllers, microprocessors, and electric units for the implementation of other functions.

The power supply unit 190 may supply power required to operate the respective components under the control of the controller 170. In particular, the power supply unit 190 may receive power from, for example, a battery (not illustrated) inside the vehicle 1.

An Audio Video Navigation (AVN) apparatus 400 may exchange data with the controller 170. The controller 170 may receive navigation information from the AVN apparatus or a separate navigation apparatus (not illustrated). Here, the navigation information may include set destination information, destination based routing information, and map information or vehicle location information related to vehicle traveling.

Meanwhile, some of the components illustrated in FIG. 1 may be not necessary to implement the vehicle 1. Accordingly, the vehicle 1 described in the present specification may include a greater or smaller number of components than those mentioned above.

Figure 2:
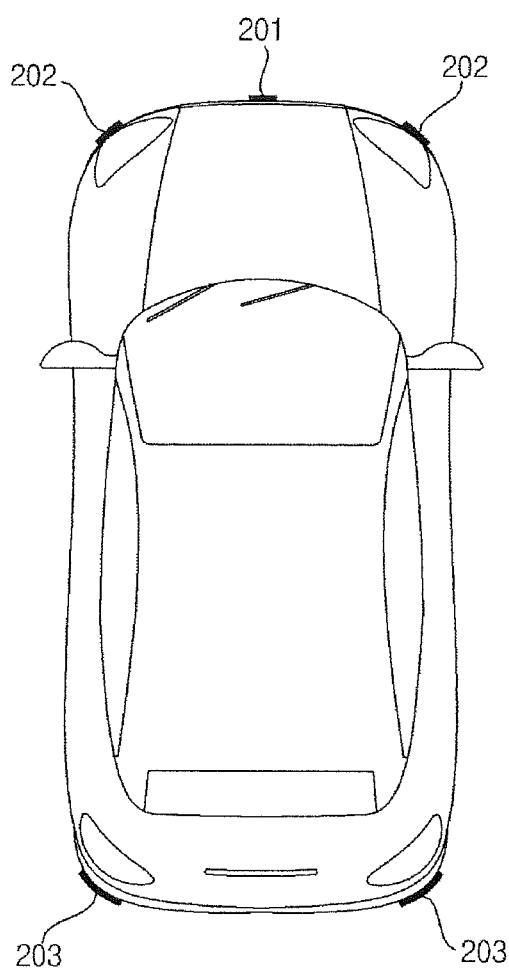
FIG. 2 is a view illustrating one exemplary vehicle with reference to FIG. 1.

FIG. 2 is a view illustrating one exemplary vehicle with reference to FIG. 1. For convenience of description, the vehicle 1 is assumed to be a four-wheeled car.

Referring to FIG. 2, the vehicle 1 may include at least one of a radar 201, Lidars 202, and ultrasonic sensors 203.

The radar 201 may be mounted at one side of the vehicle 1 and serve to emit electromagnetic waves to the vicinity of the vehicle 1 and to receive the electromagnetic waves reflected from a variety of objects that are present in the vicinity of the vehicle 1. For example, the radar 201 may acquire information related to, for example, the distance, direction, and height of any one object by measuring the time taken until the electromagnetic waves reflected by the corresponding object return thereto.

The Lidar 202 may be mounted at one side of the vehicle 1 and serve to emit laser light in the vicinity of the vehicle 1. The laser, emitted by the Lidar 202, may be scattered or reflected to thereby return to the vehicle 1. The Lidar 202 may acquire information related to physical properties such as, for example, the distance, speed, and shape of a target, which is located in the vicinity of the vehicle 1, based on the time taken until the laser returns, the strength of the laser light, variation in frequency, and variation in polarization.

The ultrasonic sensor 203 may be mounted at one side of the vehicle 1 and serve to generate ultrasonic waves in the vicinity of the vehicle 1. The ultrasonic waves, generated by the ultrasonic sensor 203, have properties of a high frequency (approx. 20 KHz or higher) and short wavelength. The ultrasonic sensor 203 may be mainly used to recognize, for example, an obstacle close to the vehicle 1.

The radar 201, the Lidars 202, and the ultrasonic sensors 203, illustrated in FIG. 2, may be sensors included in the sensing unit 160 illustrated in FIG. 1.

Figure 3:
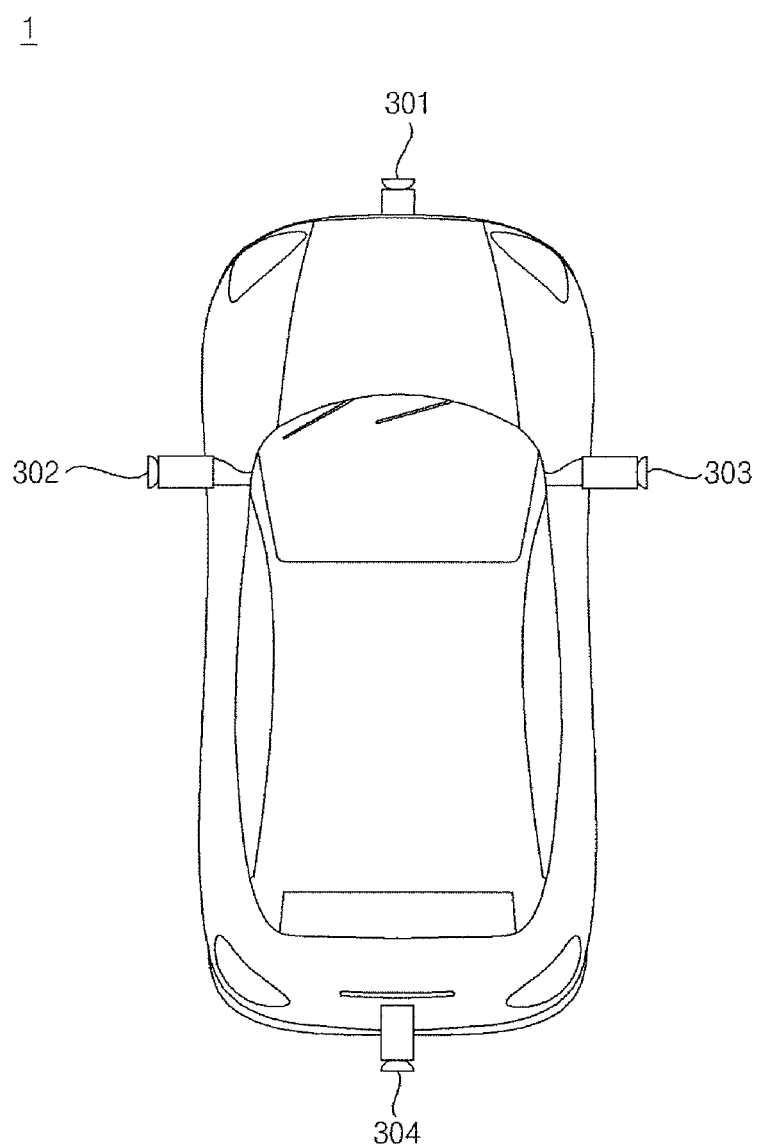
FIG. 3 is a view illustrating another exemplary vehicle with reference to FIG. 1.

FIG. 3 is a view illustrating another exemplary vehicle 1 with reference to FIG. 1. For convenience of description, the vehicle 1 is assumed to be a four-wheeled car.

Referring to FIG. 3, four cameras 301, 302, 303 and 304 may be mounted at different positions on the exterior of the vehicle 1.

The cameras 301, 302, 303 and 304 may be respectively located at the front side, the left side, the right side, and the rear side of the vehicle 1. Each of the cameras 301, 302, 303 and 304 may correspond to the camera 161 illustrated in FIG. 1.

The front camera 301 may be located near a windshield, near an emblem, or near a radiator grill.

The left camera 302 may be located inside a case enclosing a left side-view mirror. Alternatively, the left camera 302 may be located at the exterior of the case enclosing the left side-view mirror. Yet alternatively, the left camera 302 may be located at a region of the exterior of a left front door, a left rear door, or a left fender.

The right camera 303 may be located inside a case enclosing a right side-view mirror. Alternatively, the right camera 303 may be located at the exterior of the case enclosing the right side-view mirror. Yet alternatively, the right camera 303 may be located at a region at the exterior of a right front door, a right rear door, or a right fender.

Meanwhile, the rear camera 304 may be located near a rear license plate or a trunk switch.

Respective images captured by the cameras 301, 302, 303 and 304 may be transmitted to the processor 570, and the processor 570 may compose the respective images to generate a surround-view image of the vehicle 1.

Meanwhile, each of the cameras 301, 302, 303, and 304 illustrated in FIG. 3 may be the same as the camera 161 of the sensing unit 160 illustrated in FIG. 1.

In addition, although FIG. 3 illustrates the vehicle 1 as including four cameras mounted to the exterior thereof, note that the present invention is not limited as to the number of cameras, and that a greater or smaller number of cameras than those mentioned above may be mounted at different positions from the positions illustrated in FIG. 3.

Figure 4:
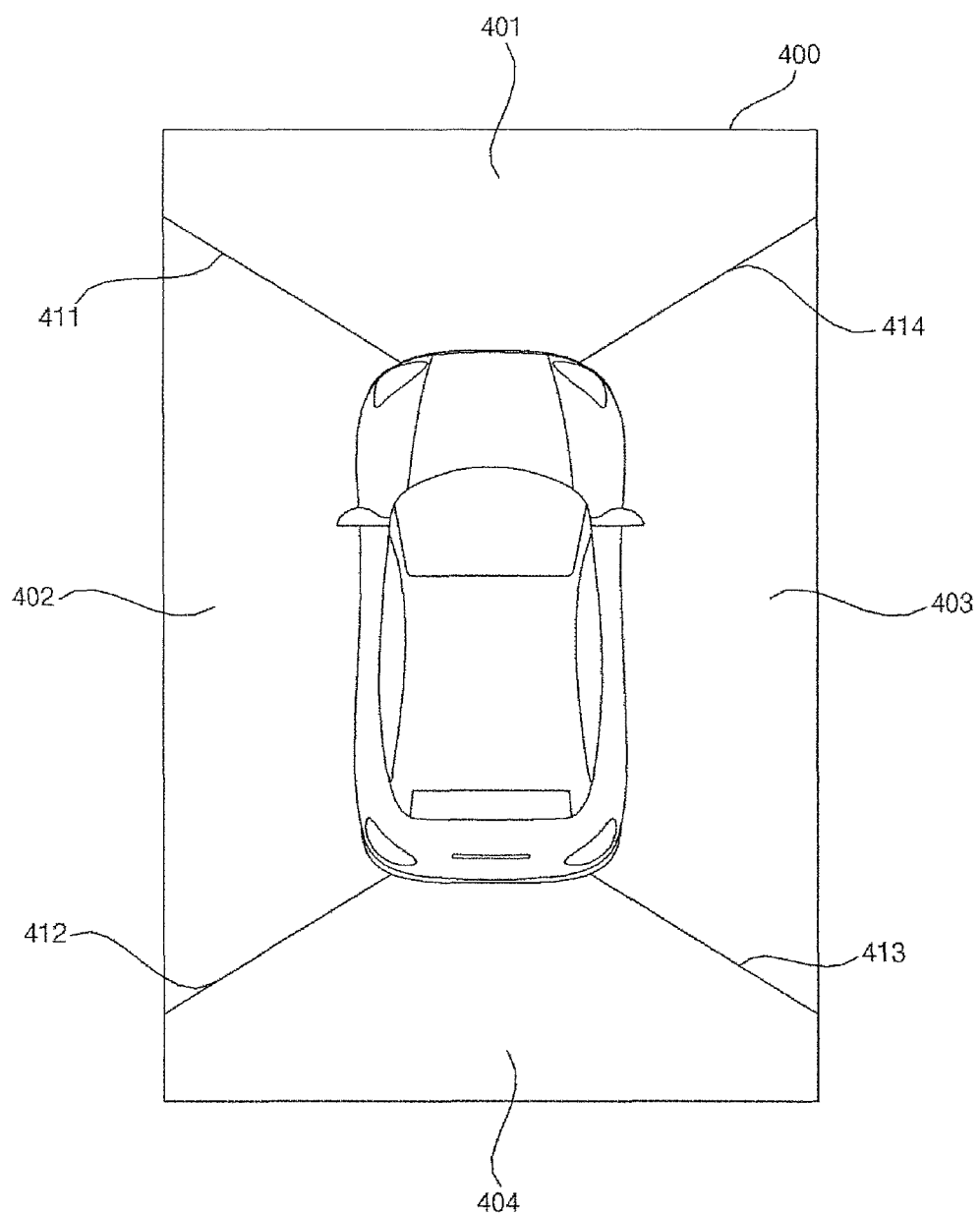
FIG. 4 is a view illustrating one exemplary image generated by a plurality of cameras illustrated in FIG. 3.

FIG. 4 is a view illustrating one exemplary image generated by the cameras 301, 302, 303 and 304 illustrated in FIG. 3.

Referring to FIG. 4, a composite image 400 may include a first image region 401 captured by the front camera 301, a second image region 402 captured by the left camera 302, a third image region 403 captured by the right camera 303, and a fourth image region 404 captured by the rear camera 304. The composite image 400 may be called an around view monitoring image.

Meanwhile, upon the generation of the composite image 400, boundary lines 411, 412, 413, and 414 are generated between respective two images included in the composite image 400. These boundaries may be subjected to image blending, for natural display thereof.

Meanwhile, the boundary lines 411, 412, 413 and 414 may be displayed at the boundaries between the respective images. In addition, the composite image 400 may include a predetermined image, indicating the vehicle 1, at the center thereof.

In addition, the composite image 400 may be displayed via a display device mounted in the space inside the vehicle 1.

Figure 5:
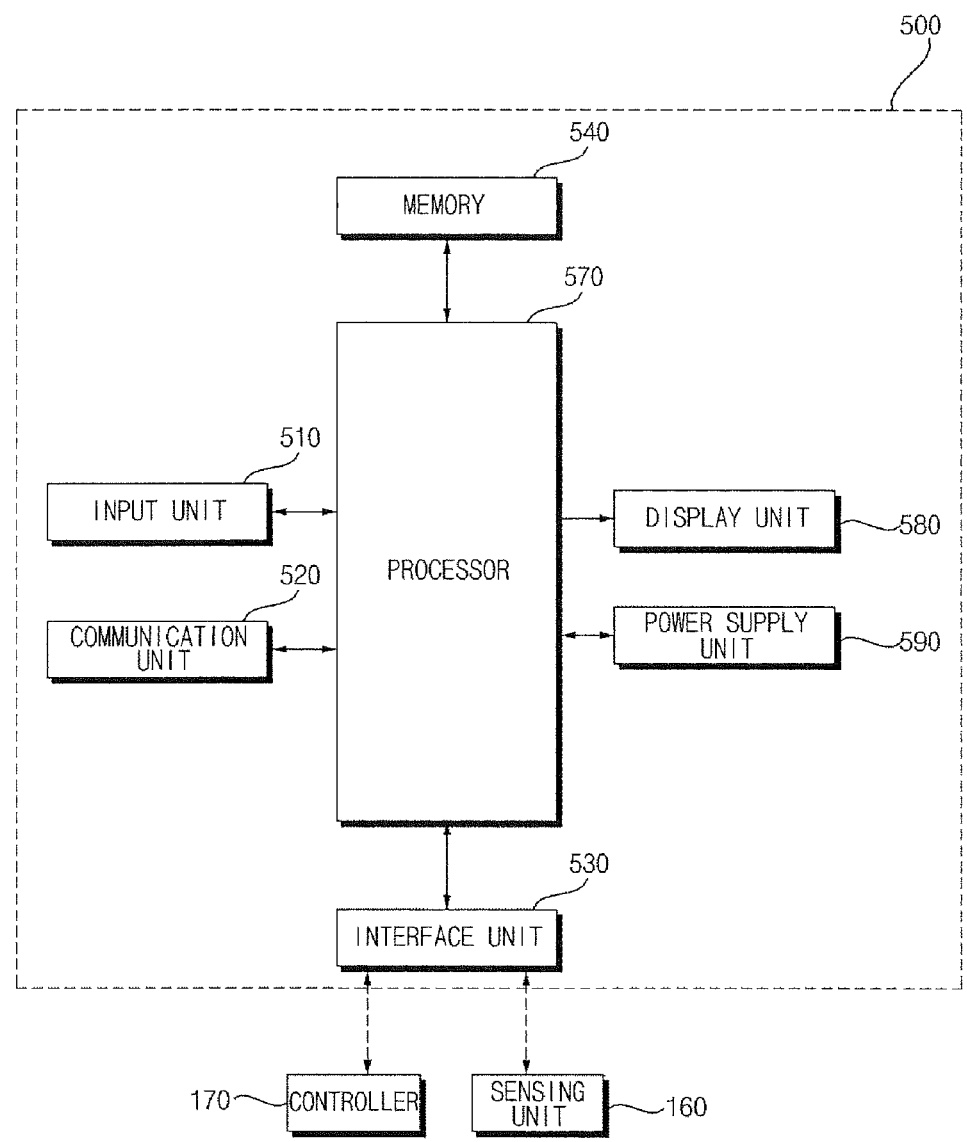
FIG. 5 is a block diagram of a driver assistance apparatus according to one embodiment of the present invention.

FIG. 5 is a block diagram of the driver assistance apparatus 500 according to one embodiment of the present invention.

The driver assistance apparatus 500 may generate vehicle associated information via computer vision based signal processing of images received from the cameras 161 and 162 illustrated in FIG. 1. Here, the vehicle associated information may include vehicle control information for the direct control of a vehicle, or vehicle traveling assistance information to guide a vehicle driver during traveling.

Here, the cameras 161 and 162 may be mono cameras or stereo cameras.

Referring to FIG. 5, the driver assistance apparatus 500 may include an input unit 510, a communication unit 520, an interface unit 530, a memory 540, a processor 570, a display unit 580, and a power supply unit 590. In some embodiments, some of the components illustrated in FIG. 5 may be omitted, or new components may be added. For example, some components included in the sensing unit 160 illustrated in FIG. 1 may be included in the driver assistance apparatus 500 rather than the vehicle 1.

The input unit 510 may include a plurality of buttons or a touchscreen. The driver may turn on the driver assistance apparatus 500 to operate the same using the buttons or the touchscreen. In addition, the input unit 510 may be used for implementation of various other input operations.

The communication unit 520 may exchange data with, for example, a mobile terminal of a passenger of the vehicle 1, an external server, or other external appliances of other vehicles in a wireless manner. In particular, the communication unit 520 may exchange data with a mobile terminal of a driver in a wireless manner. Various wireless data communication protocols such as, for example, Bluetooth, Wi-Fi, Wi-Fi direct, APiX, and NFC may be used.

The communication unit 520 may receive weather information and road traffic state information such as, for example, Transport Protocol Expert Group (TPEG) information, from the external server. Meanwhile, the communication unit 520 may transmit real-time information, acquired by the driver assistance apparatus 500, to the external appliance.

Meanwhile, when a user gets into the vehicle, the mobile terminal of the user may pair with the driver assistance apparatus 500 automatically or as the user executes a pairing application.

The communication unit 520 may receive traffic light change information from the external server. Here, the external server may be a server located in a traffic control center.

The interface unit 530 may receive vehicle associated data, or externally transmit signals processed or generated by the processor 570. To this end, the interface unit 530 may perform data communication with, for example, the controller 170 inside the vehicle 1, an Audio Video Navigation (AVN) apparatus, and the sensing unit 160 in a wired or wireless communication manner.

The interface unit 530 may receive navigation information via data communication with the controller 170 of the vehicle 1, the controller 170, the AVN apparatus, or a separate navigation apparatus. Here, the navigation information may include set destination information, destination based routing information, and map information and vehicle's current location information related to vehicle traveling. Meanwhile, the navigation information may include information regarding a vehicle's location on a road.

Meanwhile, the interface unit 530 may receive sensor information from the controller 170 or the sensing unit 160.

Here, the sensor information may include at least one selected from among vehicle traveling direction information, vehicle location information (GPS information), vehicle angle information, vehicle speed information, vehicle acceleration information, vehicle tilt information, vehicle forward/reverse information, battery information, fuel information, tire information, vehicle lamp information, vehicle interior temperature information, vehicle interior humidity information, and object information.

The sensor information may be acquired from, for example, a heading sensor, a yaw sensor, a gyro sensor, a position module, a vehicle forward/reverse sensor, a wheel sensor, a vehicle speed sensor, a vehicle body gradient sensor, a battery sensor, a fuel sensor, a tire sensor, a steering sensor based on the rotation of a steering wheel, a vehicle interior temperature sensor, a vehicle interior humidity sensor, and an object sensor (e.g., a radar, Lidar, or ultrasonic sensor). Meanwhile, the position module may include a GPS module to receive GPS information.

Meanwhile, of the above-specified sensor information, for example, vehicle traveling direction information, vehicle location information, vehicle angle information, vehicle speed information, and vehicle tilt information, which are related to vehicle traveling, may be referred to as vehicle traveling information.

The interface unit 530 may receive turn-signal information. Here, the turn-signal information may be a turn-on signal of a turn signal light for left-turn or right-turn input by the user. When an input to turn on a left or right turn signal light is received via the user input unit (124 in FIG. 1) of the vehicle 1, the interface unit 530 may receive turn-signal information for left-turn or right-turn.

The interface unit 530 may receive vehicle speed information, steering wheel rotation angle information, or gearshift information. The interface unit 530 may receive vehicle speed information, steering wheel rotation angle information, or gearshift information sensed via the sensing unit 160 of the vehicle 1. Alternatively, the interface unit 530 may receive vehicle speed information, steering wheel rotation angle information, or gearshift information from the controller 170 of the vehicle 1. Meanwhile, here, gearshift information may be information regarding the current gear position of the vehicle. For example, gearshift information may be information regarding whether the gearshift is in any one of Park (P), Reverse (R), Neutral (N), and Drive (D), or numbered gears.

The interface unit 530 may receive user input via the user input unit 124 of the vehicle 1. The interface unit 530 may receive user input from the input unit 120 of the vehicle 1, or may receive user input by way of the controller 170.

The interface unit 530 may receive information acquired from the external appliance. For example, when traffic light change information is received from the external server via the communication unit 110 of the vehicle 1, the interface unit 530 may receive the traffic light change information from the controller 170.

The memory 540 may store various data for the overall operation of the driver assistance apparatus 500 such as, for example, programs for the processing or control of the processor 570.

The memory 540 may store data for object verification. For example, when a prescribed object is detected from an image captured by the cameras 161 and 162, the memory 540 may store data to verify, using a prescribed algorithm, what does the object correspond to.

The memory 540 may store data related to traffic information. For example, when prescribed traffic information is detected from an image captured by the cameras 161 and 162, the memory 540 may store data to verify, using a prescribed algorithm, what does the traffic information correspond to.

Meanwhile, the memory 540 may be any one of various hardware storage devices such as, for example, a ROM, a RAM, an EPROM, a flash drive, and a hard drive.

The processor 570 controls the overall operation of each unit inside the driver assistance apparatus 500.

The processor 570 may process an image of view in front of the vehicle or a surround-view image of the vehicle acquired by the cameras 161 and 162. In particular, the processor 570 implements computer vision based signal processing. As such, the processor 570 may acquire an image of view in front of the vehicle or a surround-view image of the vehicle from the cameras 161 and 162, and perform object detection and object tracking based on the image. In particular, the processor 570 may perform, for example, Lane Detection (LD), Vehicle Detection (VD), Pedestrian Detection (PD), Bright-spot Detection (BD), Traffic Sign Recognition (TSR), and road surface detection during object detection.

Meanwhile, a traffic sign may mean prescribed information that may be transmitted to the driver of the vehicle 1. The traffic sign may be transmitted to the driver via a traffic light, a traffic sign, or a road surface. For example, the traffic sign may be a go signal or a stop signal for a vehicle or a pedestrian, which is output from a traffic light. For example, the traffic sign may be various symbols or text marked on a traffic sign. For example, the traffic sign may be various symbols or text marked on the road surface.

The processor 570 may detect information from a surround-view image of the vehicle acquired by the cameras 161 and 162.

The information may be vehicle traveling situation information. For example, the information may include vehicle traveling road information, traffic rule information, adjacent vehicle information, vehicle or pedestrian traffic light information, roadwork information, traffic state information, parking lot information, and lane information.

The information may be traffic information. The processor 570 may detect traffic information from any one of a traffic light, a traffic sign, and a road surface included in an image captured by the cameras 161 and 162. For example, the processor 570 may detect a go signal or a stop signal for a vehicle or a pedestrian from a traffic light included in an image. For example, the processor 570 may detect various symbols or text from a traffic sign included in an image. For example, the processor 170 may detect various symbols or text from a road surface included in an image.

The processor 570 may verify information by comparing detected information with information stored in the memory 540.

For example, the processor 570 detects a symbol or text indicating a ramp from an object included in an acquired image. Here, the object may be a traffic sign or a road surface. The processor 570 may verify ramp information by comparing the detected symbol or text with traffic information stored in the memory 540.

For example, the processor 570 detects a symbol or text indicating vehicle or pedestrian stop from an object included in an acquired image. Here, the object may be a traffic sign or a road surface. The processor 570 may verify stop information by comparing the detected symbol or text with traffic information stored in the memory 540. Alternatively, the processor 570 detects a stop line from a road surface included in an acquired image. The processor 570 may verify stop information by comparing the detected stop line with traffic information stored in the memory 540.

For example, the processor 570 may detect whether a traffic lane marker is present from an object included in an acquired image. Here, the object may be a road surface. The processor 570 may check the color of a detected traffic lane marker. The processor 570 may check whether the detected traffic lane marker is for a travel lane or a left-turn lane.

For example, the processor 570 may detect vehicle go or stop information from an object included in an acquired image. Here, the object may be a vehicle traffic light. Here, the vehicle go information may be a signal to instruct the vehicle to go straight or to turn to the left or right. The vehicle stop information may be a signal to instruct the vehicle to stop. The vehicle go information may be displayed in green and the vehicle stop information may be displayed in red.

For example, the processor 570 may detect pedestrian go or stop information from an object included in an acquired image. Here, the object may be a pedestrian traffic light. Here, the pedestrian go information may be a signal to instruct a pedestrian to cross the street at a crosswalk. The pedestrian stop information may be a signal to instruct a pedestrian to stop at a crosswalk.

Meanwhile, the processor 570 may control the zoom of the cameras 161 and 162. For example, the processor 570 may control the zoom of the cameras 161 and 162 based on an object detection result. When a traffic sign is detected, but content written on the traffic sign is not detected, the processor 570 may control the cameras 161 and 162 to zoom in.

Meanwhile, the processor 570 may receive weather information and road traffic state information, for example, Transport Protocol Expert Group (TPEG) information via the communication unit 520.

Meanwhile, the processor 570 may recognize, in real time, traffic state information around the vehicle, which has been recognized, based on stereo images, by the driver assistance apparatus 500.

Meanwhile, the processor 570 may receive, for example, navigation information from the AVN apparatus or a separate navigation apparatus (not illustrated) via the interface unit 530.

Meanwhile, the processor 570 may receive sensor information from the controller 170 or the sensing unit 160 via the interface unit 530. Here, the sensor information may include at least one selected from among vehicle traveling direction information, vehicle location information (GPS information), vehicle angle information, vehicle speed information, vehicle acceleration information, vehicle tilt information, vehicle forward/reverse information, battery information, fuel information, tire information, vehicle lamp information, vehicle interior temperature information, vehicle interior humidity information, and steering wheel rotation information.

Meanwhile, the processor 570 may receive navigation information from the controller 170, the AVN apparatus or a separate navigation apparatus via the interface unit 530.

Meanwhile, the processor 570 may be implemented using at least one of Application Specific Integrated Circuits (ASICs), Digital Signal Processors (DSPs), Digital Signal Processing Devices (DSPDs), Programmable Logic Devices (PLDs), Field Programmable Gate Arrays (FPGAs), processors, controllers, micro-controllers, microprocessors, and electric units for implementation of other functions.

The processor 570 may be controlled by the controller 170.

The display unit 580 may display various pieces of information processed in the processor 570. The display unit 580 may display an image related to the operation of the driver assistance apparatus 500. To display such an image, the display unit 580 may include a cluster or a Head Up Display (HUD) mounted at the front of the interior of the vehicle 1. Meanwhile, when the display unit 580 is a HUD, the display unit 580 may include a projector module to project an image to the windshield of the vehicle 1.

The power supply unit 590 may supply power required to operate the respective components under the control of the processor 570. In particular, the power supply unit 590 may receive power from, for example, a battery inside the vehicle 1.

Figure 6:
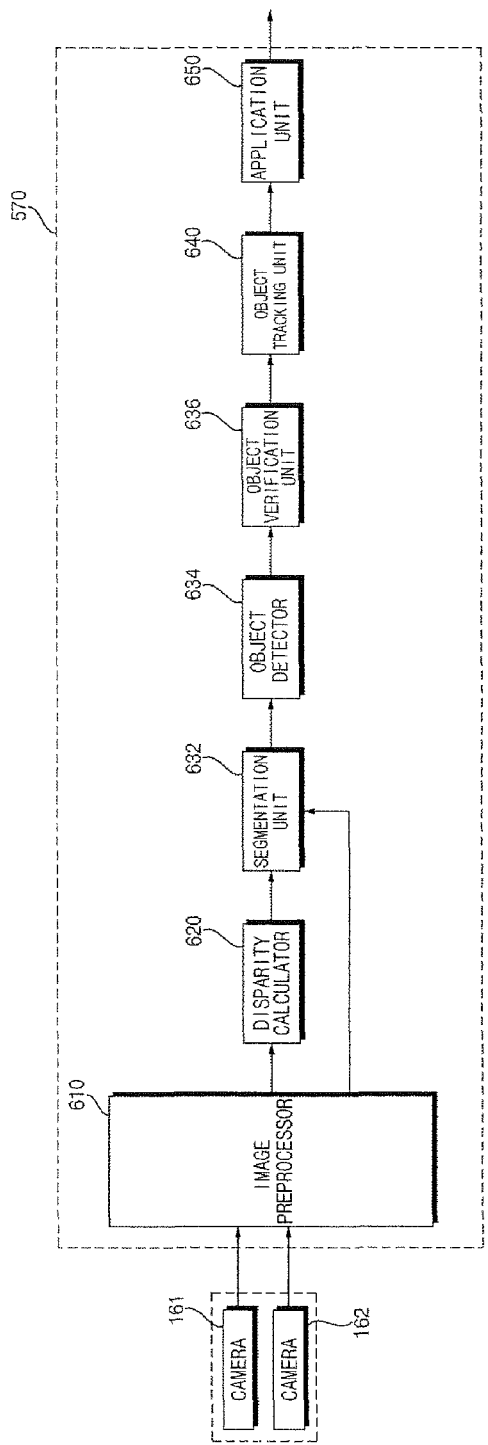
FIG. 6 is a block diagram illustrating the inner configuration of a processor illustrated in FIG. 5.

FIG. 6 is a block diagram illustrating the inner configuration of the processor 570 illustrated in FIG. 5.

Referring to FIG. 6, the processor 570 inside the driver assistance apparatus 500 may include an image preprocessor 610, a disparity calculator 620, a segmentation unit 632, an object detector 634, an object verification unit 636, an object tracking unit 640, and an application unit 650.

The image preprocessor 610 may receive images from the cameras 161 and 162 illustrated in FIG. 1, and preprocess the received images.

Specifically, the image preprocessor 610 may perform, for example, noise reduction, rectification, calibration, color enhancement, Color Space Conversion (CSC), interpolation, and camera gain control for the images. As such, the image preprocessor 610 may acquire an image more vivid than stereo images captured by the cameras 161 and 162.

The disparity calculator 620 may receive images signal-processed by the image preprocessor 610, perform stereo matching for the received images, and acquire a binocular disparity map based on the stereo matching. That is, the disparity calculator 620 may acquire binocular disparity information related to the stereo images for a view in front of the vehicle.

At this time, the stereo matching may be performed on a per pixel basis or on a per prescribed block basis of the stereo images. Meanwhile, the binocular disparity map may mean a map in which binocular parallax information between stereo images, i.e. left and right images are represented by numerical values.

The segmentation unit 632 may perform segmentation and clustering on at least one of the stereo images based on the binocular disparity information from the disparity calculator 620.

Specifically, the segmentation unit 632 may segment at least one of the stereo images into a background and a foreground based on the binocular disparity information.

For example, the segmentation unit 632 may calculate a region of the disparity map, in which the binocular disparity information is a predetermined value or less, as a background and exclude the corresponding region. In this way, a foreground may be relatively separated.

In another example, the segmentation unit 632 may calculate a region of the disparity map, in which the binocular disparity information is a predetermined value or more, as a foreground and extract the corresponding region. In this way, the foreground may be separated.

As described above, when the image is segmented into the foreground and the background based on the binocular disparity information extracted based on the stereo images, it is possible to reduce, for example, a signal processing speed and a signal processing amount during subsequent object detection.

Subsequently, the object detector 634 may detect an object based on an image segment from the segmentation unit 632.

That is, the object detector 634 may detect an object for at least one of the stereo images based on the binocular disparity information.

Specifically, the object detector 634 may detect an object for at least one of the stereo images. For example, the object detector 634 may detect an object from the foreground separated by an image segment.

Subsequently, the object verification unit 636 may classify and verify the separated object.

To this end, the object verification unit 636 may use, for example, an identification method using a neural network, a Support Vector Machine (SVM) method, an AdaBoost identification method using a Harr-like feature, or a Histograms of Oriented Gradients (HOG) method.

Meanwhile, the object verification unit 636 may compare the detected object with objects stored in the memory 540 to verify the detected object.

For example, the object verification unit 636 may verify, for example, an adjacent vehicle, a traffic lane marker, a road surface, a traffic sign, a dangerous zone, and a tunnel, which are located around the vehicle.

The object tracking unit 640 may track the verified object. For example, the object tracking unit 640 may verify an object included in sequentially acquired stereo images, calculate the motion or motion vector of the verified object, and track, for example, the movement of the corresponding object based on the calculated motion or motion vector. As such, the object tracking unit 640 may track, for example, an adjacent vehicle, a traffic lane marker, a road surface, a traffic sign, a dangerous zone, and a tunnel, which are located around the vehicle.

Subsequently, the application unit 650 may calculate, for example, the accident risk of the vehicle 1 based on various objects located around the vehicle, for example, other vehicles, traffic lane markers, road surface, and traffic signs. In addition, the application unit 650 may calculate the possibility of head-on collision with a preceding vehicle and whether or not loss of traction occurs.

In addition, the application unit 650 may output, for example, a message to notify a user of driver assistance information such as, for example, the calculated risk, collision possibility, or traction loss. Alternatively, the application unit 650 may generate a control signal, as vehicle control information, for the attitude control or traveling control of the vehicle 1.

Meanwhile, in some embodiments, some of the image preprocessor 610, the disparity calculator 620, the segmentation unit 632, the object detector 634, the object verification unit 636, the object tracking unit 640, and the application unit 650 may be included in the processor 570. In the case where the cameras 161 and 162 provide only 2-dimensional (2D) images, the disparity calculator 620 may be excluded.

Figure 7A:
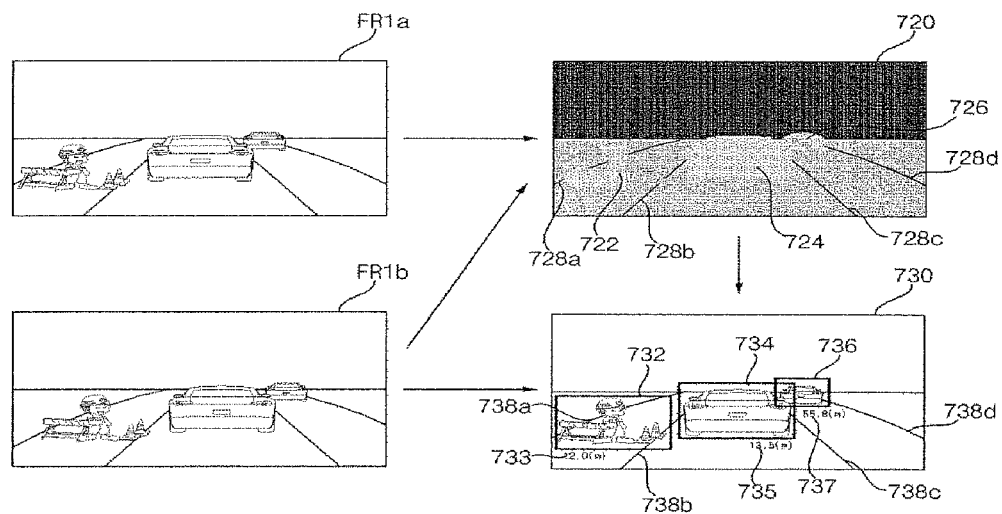
FIGS. 7A and 7B are views referenced to explain the operation of the processor illustrated in FIG. 6.
Figure 7B:
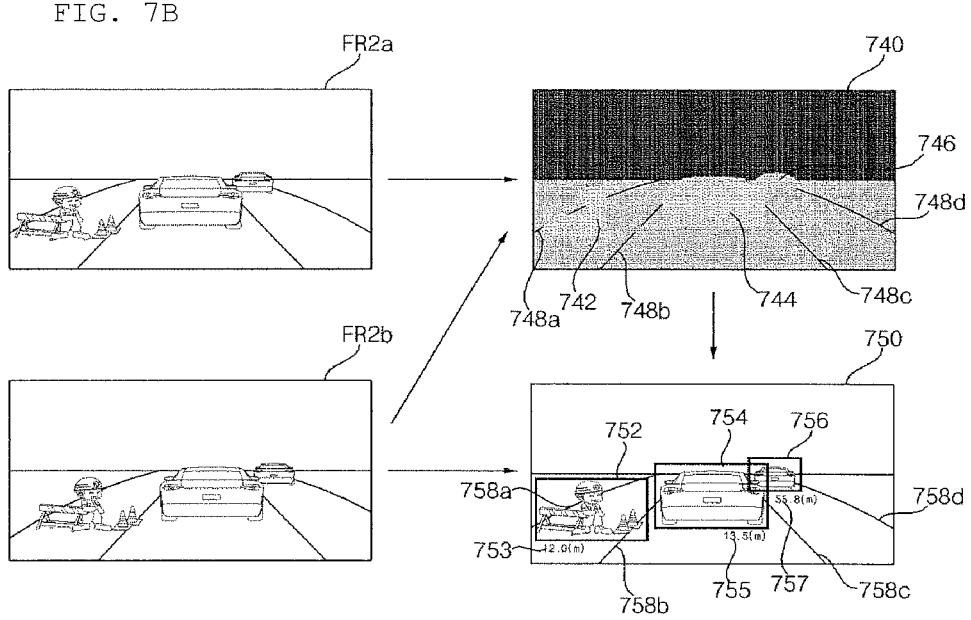

FIGS. 7A and 7B are views referenced to explain the operation of the processor 570 illustrated in FIG. 6.

FIGS. 7A and 7B are views referenced to explain an operation method of the processor 570 illustrated in FIG. 6 based on stereo images acquired respectively from first and second frame periods.

Referring first to FIG. 7A, when the cameras 161 are stereo cameras, the cameras 161 acquire stereo images during a first frame period.

The disparity calculator 620 included in the processor 570 receives stereo images FR1a and FR1b signal-processed by the image preprocessor 610 and performs stereo matching for the received stereo images FR1a and FR1b to acquire a disparity map 720.

The disparity map 720 shows a binocular disparity between the stereo images FR1a and FR1b as levels. As the disparity level is higher, the distance from the vehicle may be calculated as being shorter. As the disparity level is lower, the distance from the vehicle may be calculated as being longer.

Meanwhile, when the disparity map is displayed, the disparity map may be displayed with higher brightness as the disparity level is higher and displayed with lower brightness as the disparity level is lower.

FIG. 7A illustrates, by way of example, that, in the disparity map 720, first to fourth traffic lane markers 728a, 728b, 728c, and 728d have their own disparity levels and a roadwork zone 722, a first preceding vehicle 724, and a second preceding vehicle 726 have their own disparity levels.

The segmentation unit 632, the object detector 634, and the object verification unit 636 respectively perform segmentation, object detection, and object verification for at least one of the stereo images FR1a and FR1b based on the disparity map 720.

FIG. 7A illustrates, by way of example, that object detection and object verification for the second stereo image FR1b are performed using the disparity map 720.

That is, object detection and object verification for first to fourth traffic lane markers 738a, 738b, 738c, and 738d, a roadwork zone 732, a first preceding vehicle 734, and a second preceding vehicle 736 in an image 730 may be performed.

Next, referring to FIG. 7B, the stereo cameras 161 acquire stereo images during a second frame period.

The disparity calculator 620 included in the processor 570 receives stereo images FR2a and FR2b signal-processed by the image preprocessor 610 and performs stereo matching for the received stereo images FR2a and FR2b to acquire a disparity map 740.

FIG. 7B shows, by way of example, that, in the disparity map 740, first to fourth traffic lane markers 748a, 748b, 748c, and 748d have their own disparity levels and a roadwork zone 742, a first preceding vehicle 744, and a second preceding vehicle 746 have their own disparity levels.

The segmentation unit 632, the object detector 634, and the object verification unit 636 respectively perform segmentation, object detection, and object verification for at least one of the stereo images FR2a and FR2b based on the disparity map 740.

FIG. 7B shows, by way of example, that object detection and object verification for the second stereo image FR2b are performed using the disparity map 740.

That is, object detection and object verification for first to fourth traffic lane markers 758a, 758b, 758c, and 758d, a roadwork zone 752, a first preceding vehicle 754, and a second preceding vehicle 756 in an image 750 may be performed.

Meanwhile, the object tracking unit 640 may track verified objects by comparing FIGS. 7A and 7B with each other.

Specifically, the object tracking unit 640 may track movement of an object based on the motion or motion vectors of respective objects verified from FIGS. 7A and 7B. As such, the object tracking unit 740 may track, for example, traffic lane markers, a roadwork zone, a first preceding vehicle and a second preceding vehicle, which are located around the vehicle.

Figure 8:
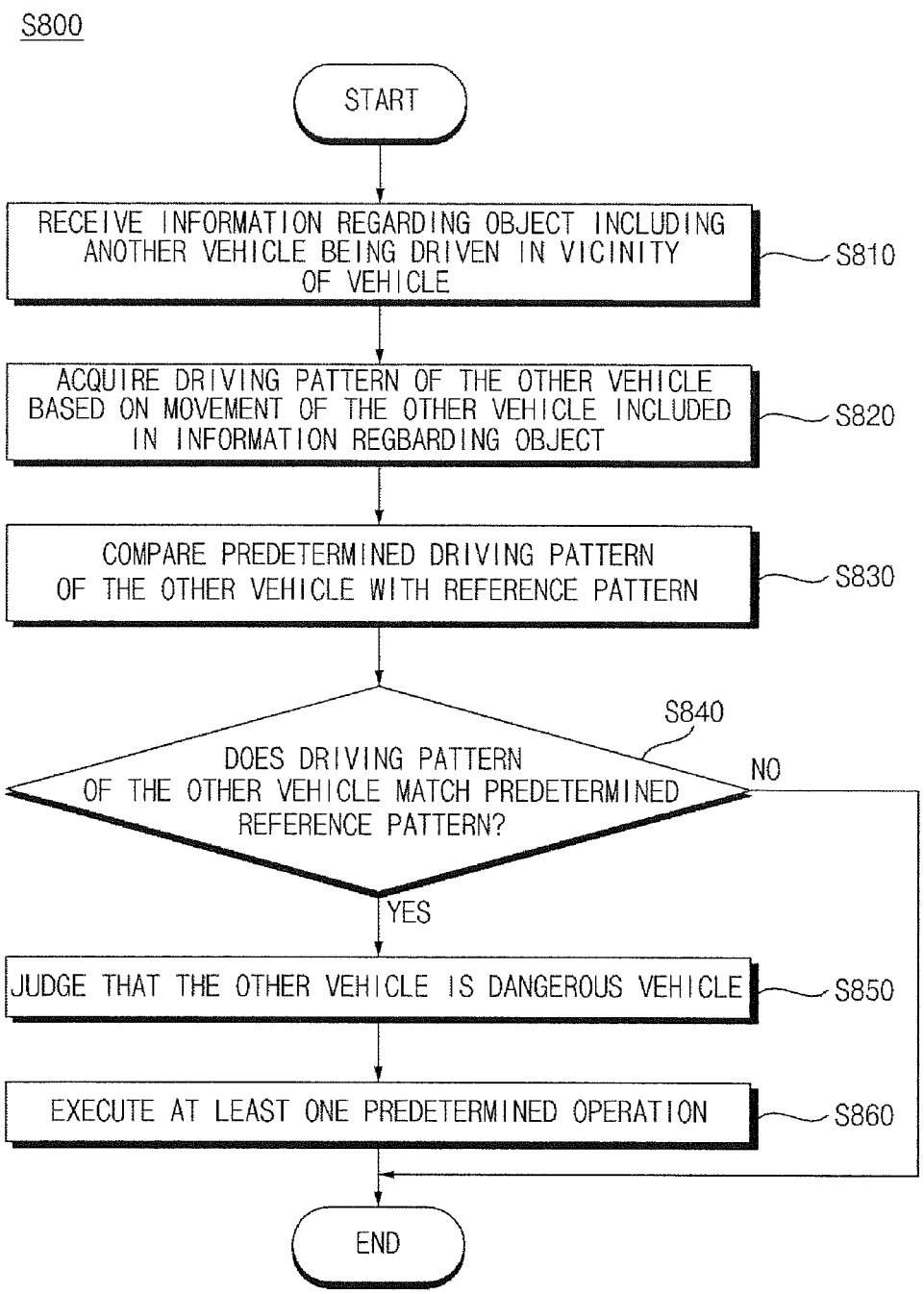
FIG. 8 is a flowchart illustrating one exemplary control method of the driver assistance apparatus according to one embodiment of the present invention.

FIG. 8 is a flowchart illustrating one exemplary control method S800 of the driver assistance apparatus 500 according to one embodiment of the present invention.

Referring to FIG. 8, in Step S810, the processor 570 of the driver assistance apparatus 500 receives information regarding an object outside the vehicle. Here, the vehicle, described with reference to FIG. 8, may be the vehicle 1 described above with reference to FIGS. 1 to 7. In addition, the object outside the vehicle includes at least one other vehicle which is being driven in the vicinity of the vehicle. The expression "the vicinity of the vehicle" may mean the region within the maximum distance in which the sensing unit 160 of the vehicle can sense objects.

Information regarding the object outside the vehicle may be acquired by at least one object detection sensor included in the sensing unit 160 of the vehicle. For example, the sensing unit 160 may include at least one of a radar, Lidar, and ultrasonic sensor, and may sense a variety of objects that are present in the vicinity of the vehicle, thereby providing the processor 570 with electrical signals corresponding to the sensed results.

Here, the information regarding the object may include, for example, the kinds of objects (e.g., pedestrians, other vehicles, buildings, and traffic lane markers), the movement of objects (e.g., movement direction, lateral velocity, longitudinal velocity, and path), distances from objects, and the sizes of objects.

In Step S820, the processor 570 acquires the driving pattern of the other vehicle based on the movement of the other vehicle included in the information regarding the object received via Step S810. Specifically, the processor 570 may acquire the driving pattern of the other vehicle by comparing pieces of information regarding the movement of the other vehicle, sequentially provided as time passes with each other, at a prescribed time interval. For example, the processor 570 may determine the first movement of the other vehicle at a first point in time, and may determine the second movement of the other vehicle at a second point in time, and thereafter, may acquire the difference between the first movement and the second movement, thereby acquiring the driving pattern of the other vehicle based on the difference between the first movement and the second movement. At this time, the first point in time and the second point in time may be spaced apart from each other by a predetermined time interval (e.g., 0.1 second). The driving pattern of the other vehicle acquired by the processor 570 may include, for example, the number of times that the other vehicle suddenly reduces its speed, the number of times that the other vehicle suddenly accelerates, the number of times that the other vehicle makes a lane change, and the number of times that the other vehicle changes its heading direction during a prescribed time period (e.g., 3 seconds), and the average distance between the vehicle and the other vehicle.

In Step S830, the processor 570 compares the driving pattern of the other vehicle, acquired via Step S820, with a reference pattern. Here, the reference pattern may be a driving pattern that is preset in at least one of the processor 570 and the memory 540 in order to judge whether the other vehicle in the vicinity of the vehicle is being driven abnormally. The reference pattern may include at least one critical value on a per item basis for judging whether the driving pattern of the other vehicle is abnormal. The reference pattern may include, for example, a critical value (e.g., 3 times) about the number of times that the other vehicle suddenly reduces its speed during a prescribed time period, a critical value (e.g., 7 times) about the number of times that the other vehicle suddenly accelerates during a prescribed time period, a critical value (e.g., 4 times) about the number of times that the other vehicle makes a lane change, a critical value (e.g., 4 times) about the number of times that the other vehicle changes its heading direction, and a critical value about the average distance (e.g., 20 m) between the vehicle and the other vehicle.

In Step S840, the processor 570 judges whether the driving pattern of the other vehicle matches the reference pattern based on the result of the comparison performed in Step S830. For example, the processor 570 may judge that the driving pattern of the other vehicle matches the reference pattern when any one item of the driving pattern of the other vehicle (e.g., the number of times that the other vehicle changes its heading direction) exceeds the critical value of the same item of the reference pattern. In another example, the processor 570 may judge that the driving pattern of the other vehicle matches the reference pattern when two or more items of the driving pattern of the other vehicle (e.g., the number of times that the other vehicle makes a lane change and the number of times that the other vehicle changes its heading direction) exceed the critical values of the same two or more items of the reference pattern.

Upon judging in Step S840 that the driving pattern of the other vehicle matches the reference pattern, in Step S850, the processor 570 performs an operation of judging that the other vehicle is a dangerous vehicle. In the present invention, the expression "dangerous vehicle" may mean another vehicle that has a likelihood of colliding with the vehicle or that is an obstacle to the normal driving of the vehicle.

On the other hand, upon judging in Step S840 that the driving pattern of the other vehicle does not match the reference pattern, the control method S800 may end.

In Step S860, the processor 570 executes at least one predetermined operation in response to the driving pattern of the other vehicle that is judged to be a dangerous vehicle. At this time, the operation executed by the processor 570 may be selected based on the difference between the driving pattern of the other vehicle and the reference pattern. For example, as the difference between the driving pattern of the other vehicle and the reference pattern increases, a greater number of operations may be executed by the processor 570.

The operation executed in Step S860 described above may include a first operation. The first operation may be an operation of notifying the vehicle driver of information regarding the other vehicle that is judged to be a dangerous vehicle. For example, the processor 570 may output a warning signal indicating the presence of the other vehicle that is being driven abnormally in the vicinity of the vehicle and has a likelihood of colliding with the vehicle. The warning signal may be output in a visual, audible, or tactile manner.

Alternatively, the operation executed in Step S860 may include a second operation. The second operation may be an operation of predicting what behavior will be taken by the other vehicle in the future based on the driving pattern of the other vehicle that is judged to be a dangerous vehicle. In one example, the processor 570 may predict the direction in which the other vehicle will move from its current position.

Alternatively, the operation executed in Step S860 may include a third operation. The third operation may be an operation of controlling the driving state of the vehicle based on the behavior of the other vehicle predicted via the second operation described above. For example, the processor 570 may reduce the speed of the vehicle so as to increase the distance from the other vehicle, or may move the vehicle from the lane in which the other vehicle is being driven to a different lane.

Alternatively, the operation executed in Step S860 may include a fourth operation. The fourth operation may be an operation of providing other vehicles that are being driven in the vicinity of the vehicle with information regarding the other vehicle that is judged to be a dangerous vehicle. For example, the processor 570 may transmit a message, indicating that the other vehicle is being driven abnormally, to other vehicles via inter-vehicular communication. In another example, after graphic processing of information indicating that the other vehicle is being driven abnormally, the processor 570 may control a display of the vehicle to display the graphic information so that it can be checked from the outside. In this case, the display may be mounted to the exterior of the vehicle.

Alternatively, the operation executed in Step S860 may include a fifth operation. The fifth operation may be an operation of changing the searched and set route of the vehicle to another route.

Alternatively, the operation executed in Step S860 may include a sixth operation. The sixth operation may be an operation of assorting a plurality of driving images, provided from at least one camera mounted to the vehicle, into a driving image including the other vehicle and a driving image not including the other vehicle, and separately storing the images. For this purpose, a storage region (e.g., a folder) for storing the driving image including the other vehicle may be allocated in the memory 540.

Figure 9:
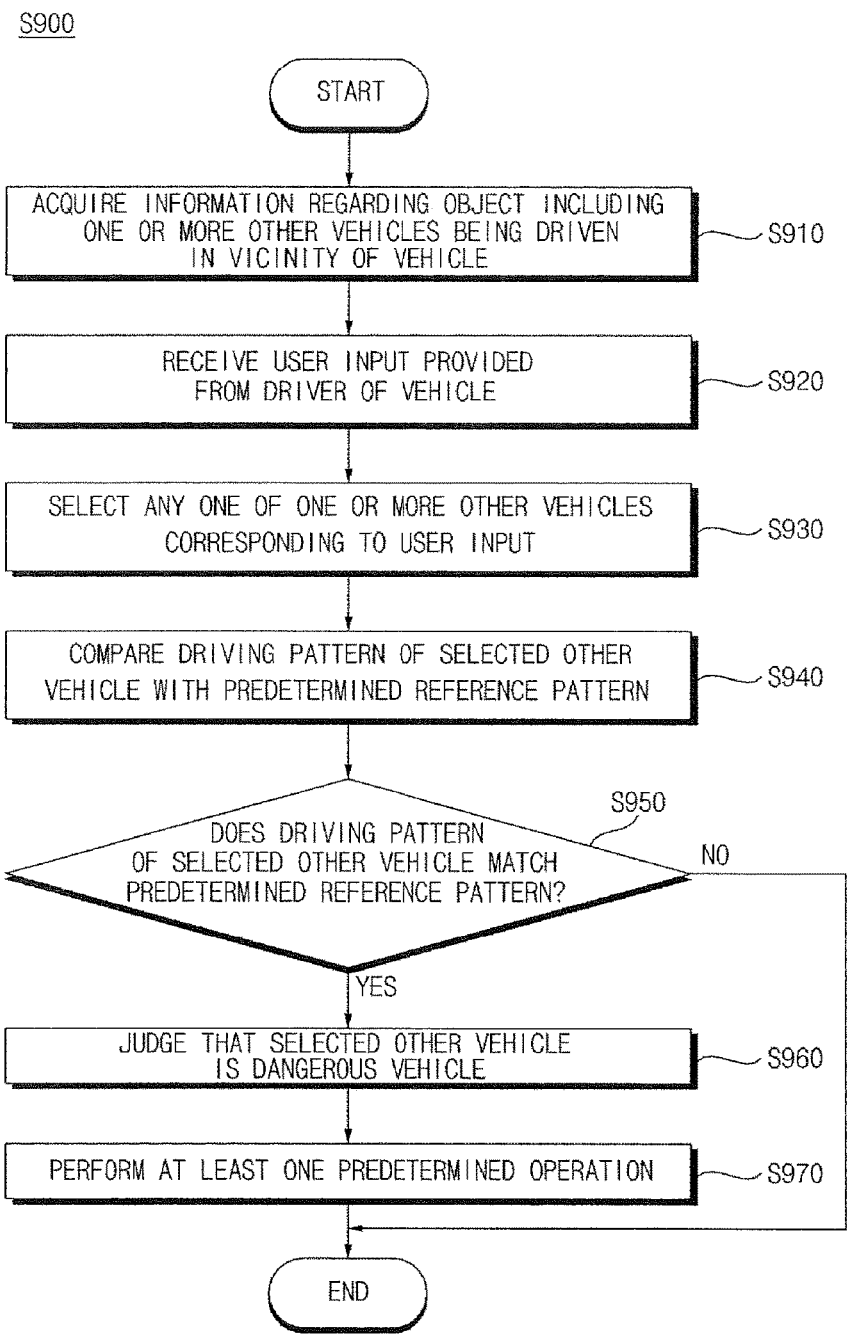
FIG. 9 is a flowchart illustrating another exemplary control method of the driver assistance apparatus according to one embodiment of the present invention.

FIG. 9 is a flowchart illustrating another exemplary control method S900 of the driver assistance apparatus 500 according to one embodiment of the present invention.

Referring to FIG. 9, in Step S910, the processor 570 of the driver assistance apparatus 500 receives information regarding an object outside the vehicle. Here, the vehicle, described with reference to FIG. 9, may be the vehicle 1 described above with reference to FIGS. 1 to 7. In addition, the object outside the vehicle includes at least one other vehicle which is being driven in the vicinity of the vehicle. The expression "the vicinity of the vehicle" may mean the region within the maximum distance in which the sensing unit 160 of the vehicle can sense objects.

Information regarding the object outside the vehicle may be acquired by at least one object detection sensor included in the sensing unit 160 of the vehicle. For example, the sensing unit 160 may include at least one of a radar, Lidar, and ultrasonic sensor, and may sense a variety of objects that are present in the vicinity of the vehicle, thereby providing the processor 570 with electrical signals corresponding to the sensed results.

Here, the information regarding the object may include, for example, the kinds of objects (e.g., pedestrians, other vehicles, buildings, and traffic lane markers), the movement of objects (e.g., movement direction, lateral velocity, longitudinal velocity, and path), distances from objects, and the sizes of objects.

In Step S920, the processor 570 receives user input provided from the driver of the vehicle. Here, the user input may be any of various types such as, for example, voice, gesture, or touch. In one example, the processor 570 may receive a 3-dimensional (3D) indoor image from an indoor camera (e.g., infrared camera) mounted at one side inside the vehicle, and may recognize a hand gesture of the driver from the indoor image. In another example, the processor 570 may receive an electrical signal corresponding to a voice command of the driver from the microphone 123 mounted at one side inside the vehicle.

In Step S930, the processor 570 may, in response to the user input received in Step S920, select any one vehicle from among one or more vehicles included in the object described above in Step S910. In one example, when the user input is the driver's hand gesture, the processor 570 may determine the direction in which the driver's hand gesture is pointing, and may select the other vehicle located in the direction indicated by the hand gesture.

In Step S940, the processor 570 performs an operation of comparing the driving pattern of the other vehicle selected in Step S930 with a reference pattern. Here, the driving pattern of the other vehicle may be acquired based on the movement of the other vehicle as described above with reference to FIG. 8. In addition, the reference pattern may be a driving pattern preset in at least one of the processor 570 and the memory 540 in order to judge whether the other vehicle in the vicinity of the vehicle is being driven abnormally. The reference pattern may include at least one critical value on a per item basis for judging whether the driving pattern of the other vehicle is abnormal. For example, the reference pattern may include, for example, a critical value (e.g., 3 times) about the number of times that the other vehicle suddenly reduces its speed during a prescribed time period, a critical value (e.g., 7 times) about the number of times that the other vehicle suddenly accelerates during a prescribed time period, a critical value (e.g., 4 times) about the number of times that the other vehicle makes a lane change, a critical value (e.g., 4 times) about the number of times that the other vehicle changes its heading direction, and a critical value (e.g., 20 m) about the average distance between the vehicle and the other vehicle.

In Step S950, the processor 570 judges whether the driving pattern of the selected other vehicle matches the reference pattern based on the result of the comparison performed in Step S940. For example, the processor 570 may judge that the driving pattern of the other vehicle matches the reference pattern when any one item of the driving pattern of the other vehicle (e.g., the number of times that the other vehicle changes its heading direction) exceeds the critical value of the same item of the reference pattern. In another example, the processor 570 may judge that the driving pattern of the other vehicle matches the reference pattern when two or more items of the driving pattern of the other vehicle (e.g., the number of times that the other vehicle makes a lane change and the number of times that the other vehicle changes its heading direction) exceed the critical values of the same two or more items of the reference pattern.

Upon judging in Step S950 that the driving pattern of the other vehicle matches the reference pattern, in Step S960, the processor 570 performs an operation of judging that the other vehicle is a dangerous vehicle. On the other hand, upon judging in Step S950 that the driving pattern of the other vehicle does not match the reference pattern, the control method S900 may end.

In Step S970, the processor 570 executes at least one predetermined operation in response to the driving pattern of the other vehicle that is judged to be a dangerous vehicle. At this time, the operation executed by the processor 570 may be selected based on the difference between the driving pattern of the other vehicle and the reference pattern. For example, as the difference between the driving pattern of the vehicle and the reference pattern increases, a greater number of operations may be executed by the processor 570.

The operation executed in Step S970 described above may include a first operation. The first operation may be an operation of notifying the vehicle driver of information regarding the other vehicle that is judged to be a dangerous vehicle. For example, the processor 570 may output a warning signal indicating the presence of the other vehicle that is being driven abnormally in the vicinity of the vehicle and has a likelihood of colliding with the vehicle. The warning signal may be output in a visual, audible, or tactile manner.

Alternatively, the operation executed in Step S970 may include a second operation. The second operation may be an operation of predicting what behavior will be taken by the other vehicle in the future based on the driving pattern of the other vehicle that is judged to be a dangerous vehicle. In one example, the processor 570 may predict the direction in which the other vehicle will move from its current position.

Alternatively, the operation executed in Step S970 may include a third operation. The third operation may be an operation of controlling the driving state of the vehicle based on the behavior of the other vehicle predicted via the second operation described above. For example, the processor 570 may reduce the speed of the vehicle so as to increase the distance from the other vehicle, or may move the vehicle from the lane in which the other vehicle is being driven to a different lane.

Alternatively, the operation executed in Step S970 may include a fourth operation. The fourth operation may be an operation of providing other vehicles that are being driven in the vicinity of the vehicle with information regarding the other vehicle that is judged to be a dangerous vehicle. For example, the processor 570 may transmit a message, indicating that the other vehicle is being driven abnormally, to other vehicles via inter-vehicular communication. In another example, after graphic processing of information indicating that the other vehicle is being driven abnormally, the processor 570 may control a display of the vehicle to display the graphic information so that it can be checked from the outside. In this case, the display may be mounted to the exterior of the vehicle.

Alternatively, the operation executed in Step S970 may include a fifth operation. The fifth operation may be an operation of changing the searched and set route of the vehicle to another route.

Alternatively, the operation executed in Step S970 may include a sixth operation. The sixth operation may be an operation of assorting a plurality of driving images provided from at least one camera mounted to the vehicle into a driving image including the other vehicle and a driving image not including the other vehicle, and separately storing the images. For this purpose, a storage region (e.g., a folder) for storing the driving image including the other vehicle may be allocated in the memory 540.

Figure 10:
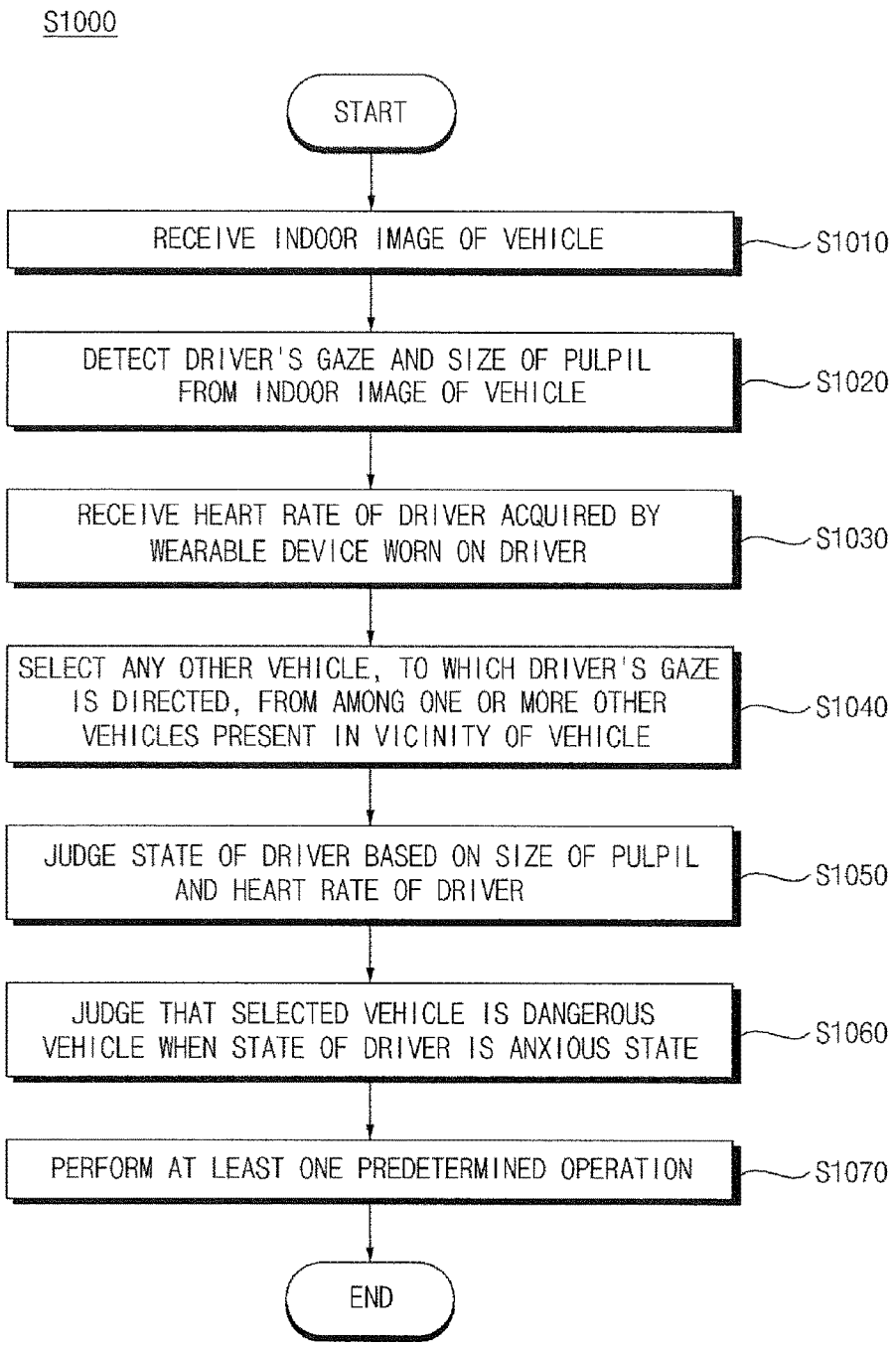
FIG. 10 is a flowchart illustrating still another exemplary control method of the driver assistance apparatus according to one embodiment of the present invention.

FIG. 10 is a flowchart illustrating still another exemplary control method S1000 of the driver assistance apparatus 500 according to one embodiment of the present invention.

Referring to FIG. 10, the processor 570 of the driver assistance apparatus 500 may receive an indoor image in Step S1010, and may detect the driver's gaze and the size of the pupils from the indoor image in Step S1020. Here, the vehicle, described with reference to FIG. 10, may be the vehicle 1 described above with reference to FIGS. 1 to 7. In one example, the processor 570 may receive a 3D indoor image from the camera 162 mounted at one side inside the vehicle, and may detect the driver's gaze and the size of the pupils by processing the indoor image. At this time, the camera 162 may include at least one of a mono-camera, a stereo-camera, an infrared camera, and a depth camera.

In Step S1030, the processor 570 may receive the heart rate of the driver. In this case, the heart rate of the driver may be acquired by a wearable device 600 worn on part of the driver's body. For example, the wearable device 600 may transmit, based on short range wireless communication, information regarding the heart rate of the driver measured using a heart rate sensor included therein to the communication unit 520 of the driver assistance apparatus 500, and the processor 570 may receive the heart rate of the driver received by the communication unit 110.

In Step S1040, the processor 570 may select any one vehicle, located in the direction in which the driver's gaze detected in Step S1020 is directed, from among one or more vehicles that are being driven in the vicinity of the vehicle. To this end, the processor 570 may first perform a process of identifying at least one other vehicle that is being driven in the vicinity of the vehicle based on the information regarding the object outside the vehicle provided from the sensing unit 160.

In Step S1050, the processor 570 may determine the driver's state based on the size of the pupils and the heart rate of the driver. At this time, at least one critical value for the determination of the driver's state may be preset in the processor 570. For example, a first critical value about the size of the pupils and a second critical value about the heart rate may be preset in the processor 570. The processor 570 may compare the size of the driver's pupils with the first critical value and the heart rate of the driver with the second critical value, and thereafter may determine the driver's state based on the results of the two comparisons. Here, the expression "driver's state" may mean the driver's mental state.

In one example, when the size of the driver's pupils is below the first critical value and the heart rate of the driver is below the second critical value, the processor 570 may determine that the driver's state is the stable state. In another example, when the size of the driver's pupils is below the first critical value and the heart rate of the driver is equal to or greater than the second critical value, the processor 570 may determine that the driver's state is the normal state. In still another example, when the size of the driver's pupils is equal to or greater than the first critical value and the heart rate of the driver is below the second critical value, the processor 570 may determine that the driver's state is the normal state. In a further example, when the size of the driver's pupils is equal to or greater than the first critical value and the heart rate of the driver is equal to or greater than the second critical value, the processor 570 may determine that the driver's state is the anxious state.

Meanwhile, Step S1050 may be performed only in the case where the driver's gaze is continuously directed to the other vehicle selected in Step S1040.

Upon judging in Step S1050 that the driver' state is the anxious state, in Step S1060, the processor 570 judges that the other vehicle selected based on the driver's gaze is a dangerous vehicle. That is, the processor 570 may judge that the driver feels anxiety due to the movement of the other vehicle.

In Step S1070, the processor 570 executes at least one predetermined operation in response to the driving pattern of the other vehicle that is judged to be a dangerous vehicle. Specifically, the operation executed in Step S1070 may include a first operation. The first operation may be an operation of notifying the vehicle driver of information regarding the other vehicle that is judged to be a dangerous vehicle. For example, the processor 570 may output a warning signal indicating the presence of the other vehicle that is being driven abnormally in the vicinity of the vehicle and has a likelihood of colliding with the vehicle. The warning signal may be output in a visual, audible, or tactile manner.

Alternatively, the operation executed in Step S1070 may include a second operation. The second operation may be an operation of predicting what behavior will be taken by the other vehicle in the future based on the driving pattern of the other vehicle that is judged to be a dangerous vehicle. In one example, the processor 570 may predict the direction in which the other vehicle will move from its current position.

Alternatively, the operation executed in Step S1070 may include a third operation. The third operation may be an operation of controlling the driving state of the vehicle based on the behavior of the other vehicle predicted via the second operation described above. For example, the processor 570 may reduce the speed of the vehicle so as to increase the distance from the other vehicle, or may move the vehicle from the lane in which the other vehicle is being driven to a different lane.

Alternatively, the operation executed in Step S1070 may include a fourth operation. The fourth operation may be an operation of providing other vehicles that are being driven in the vicinity of the vehicle with information regarding the other vehicle that is judged to be a dangerous vehicle. For example, the processor 570 may transmit a message, indicating that the other vehicle is being driven abnormally, to other vehicles via inter-vehicular communication. In another example, after graphic processing of information indicating that the other vehicle is being driven abnormally, the processor 570 may control a display of the vehicle to display the graphic information so that it can be checked from the outside. In this case, the display may be mounted to the exterior of the vehicle.

Alternatively, the operation executed in Step S1070 may include a fifth operation. The fifth operation may be an operation of changing the searched and set route of the vehicle to another route.

Alternatively, the operation executed in Step S1070 may include a sixth operation. The sixth operation may be an operation of assorting a plurality of driving images provided from at least one camera mounted to the vehicle into a driving image including the other vehicle and a driving image not including the other vehicle and separately storing the images. For this purpose, a storage region (e.g., a folder) for storing the driving image including the other vehicle may be allocated in the memory 540.

Figure 11:
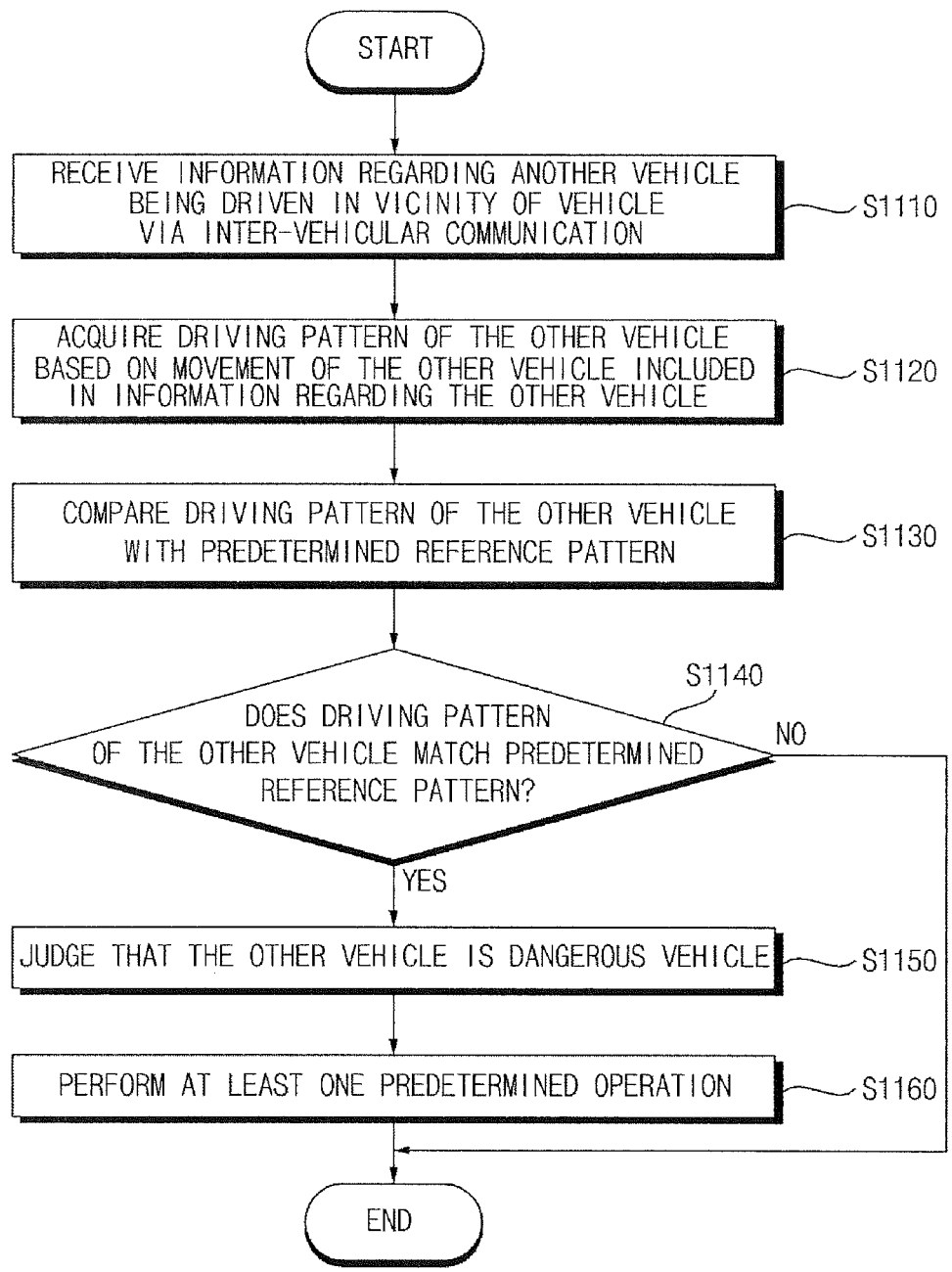
FIG. 11 is a flowchart illustrating a further exemplary control method of the driver assistance apparatus according to one embodiment of the present invention.

FIG. 11 is a flowchart illustrating a further exemplary control method S1100 of the driver assistance apparatus 500 according to one embodiment of the present invention.

Referring to FIG. 11, in Step S1110, the processor 570 of the driver assistance apparatus 500 receives information regarding another vehicle that is being driven in the vicinity of the vehicle via inter-vehicular communication.

Here, the vehicle, described with reference to FIG. 11, may be the vehicle 1 described above with reference to FIGS. 1 to 7. In addition, the expression "the vicinity of the vehicle" may mean the region within the maximum distance in which the sensing unit 160 of the vehicle can sense the object. Information regarding the other vehicle may be information transmitted from other vehicles that are being driven in the vicinity of the vehicle. In addition, information regarding the other vehicle may include information regarding the movement of the other vehicle.

In Step S1120, the processor 570 acquires the driving pattern of the other vehicle based on the movement of the other vehicle included in the information regarding the object received via Step S1110. Specifically, the processor 570 may acquire the driving pattern of the other vehicle based on information regarding the movement of the other vehicle sequentially received via inter-vehicular communication. For example, the processor 570 may judge the first movement of the other vehicle at a first point in time and may judge the second movement of the other vehicle at a second point in time, and thereafter, may acquire the difference between the first movement and the second movement, thereby acquiring the driving pattern of the other vehicle based on the difference between the first movement and the second movement. At this time, the first point in time and the second point in time may be spaced apart from each other by a predetermined time interval (e.g., 0.1 second). The driving pattern of the other vehicle acquired by the processor 570 may include, for example, the number of times that the other vehicle suddenly reduces speed, the number of times that the other vehicle suddenly accelerates, the number of times that the other vehicle makes a lane change, and the number of times that the other vehicle changes its heading direction during a prescribed time period (e.g., 3 seconds) with respect to the other vehicle, and the average distance between the vehicle and the other vehicle.

In Step S1130, the processor 570 compares the driving pattern of the other vehicle, acquired via Step S1120, with a reference pattern. Here, the reference pattern may be a driving pattern that is preset in at least one of the processor 570 and the memory 540 in order to judge whether the other vehicle in the vicinity of the vehicle is being driven abnormally. The reference pattern may include at least one critical value on a per item basis for judging whether the driving pattern of the other vehicle is abnormal. For example, the reference pattern may include, for example, a critical value (e.g., 3 times) about the number of times that the other vehicle suddenly reduces its speed during a prescribed time period, a critical value (e.g., 7 times) about the number of times that the other vehicle suddenly accelerates during a prescribed time period, a critical value (e.g., 4 times) about the number of times that the other vehicle makes a lane change, a critical value (e.g., 4 times) about the number of times that the other vehicle changes the heading direction, and a critical value (e.g., 20 m) about the average distance between the vehicle and the other vehicle.

In Step S1140, the processor 570 judges whether the driving pattern of the other vehicle matches the reference pattern based on the result of the comparison performed in Step S1130. For example, the processor 570 may judge that the driving pattern of the other vehicle matches the reference pattern when any one item of the driving pattern of the other vehicle (e.g., the number of times that the other vehicle changes the heading direction) exceeds the critical value of the same item of the reference pattern. In another example, the processor 570 may judge that the driving pattern of the other vehicle matches the reference pattern when two or more items of the driving pattern of the other vehicle (e.g., the number of times that the other vehicle makes a lane change and the number of times that the other vehicle changes its heading direction) exceed the critical values of the same two or more items of the reference pattern.

Upon judging in Step S1140 that the driving pattern of the other vehicle matches the reference pattern, in Step S1150, the processor 570 performs an operation of judging that the other vehicle is a dangerous vehicle. On the other hand, upon judging in Step S1140 that the driving pattern of the other vehicle does not match the reference pattern, the control method S1100 may end.

In Step S1160, the processor 570 executes at least one predetermined operation in response to the driving pattern of the other vehicle that is judged to be a dangerous vehicle. At this time, the operation executed by the processor 570 may be selected based on the difference between the driving pattern of the other vehicle and the reference pattern. For example, as the difference between the driving pattern of the vehicle and the reference pattern increases, a greater number of operations may be executed by the processor 570.

The operation executed in Step S1160 described above may include a first operation. The first operation may be an operation of notifying the vehicle driver of information regarding the other vehicle that is judged to be a dangerous vehicle. For example, the processor 570 may output a warning signal indicating the presence of the other vehicle that is being driven abnormally in the vicinity of the vehicle and has a likelihood of colliding with the vehicle. The warning signal may be output in a visual, audible, or tactile manner.

Alternatively, the operation executed in Step S1160 may include a second operation. The second operation may be an operation of predicting what behavior will be taken by the other vehicle in the future based on the driving pattern of the other vehicle that is judged to be a dangerous vehicle. In one example, the processor 570 may predict the direction in which the other vehicle will move from its current position.

Alternatively, the operation executed in Step S1160 may include a third operation. The third operation may be an operation of controlling the driving state of the vehicle based on the behavior of the other vehicle predicted via the second operation described above. For example, the processor 570 may reduce the speed of the vehicle so as to increase the distance from the other vehicle, or may move the vehicle from the lane in which the other vehicle is being driven to a different lane.

Alternatively, the operation executed in Step S1160 may include a fourth operation. The fourth operation may be an operation of providing other vehicles that are being driven in the vicinity of the vehicle with information regarding the other vehicle that is judged to be a dangerous vehicle. For example, the processor 570 may transmit a message, indicating that the other vehicle is being driven abnormally, to other vehicles via inter-vehicular communication. In another example, after graphic processing of information indicating that the other vehicle is being driven abnormally, the processor 570 may control a display of the vehicle to display the graphic information so that it can be checked from the outside. In this case, the display may be mounted to the exterior of the vehicle.

Alternatively, the operation executed in Step S1160 may include a fifth operation. The fifth operation may be an operation of changing the searched and set route of the vehicle to another route.

Alternatively, the operation executed in Step S1160 may include a sixth operation. The sixth operation may be an operation of assorting and separately storing a plurality of driving images provided from at least one camera mounted to the vehicle into a driving image including the other vehicle and a driving image not including the other vehicle. For this purpose, a storage region (e.g., a folder) for storing the driving image including the other vehicle may be allocated in the memory 540.

Meanwhile, at least one of a plurality of blocks (i.e. steps) included in the control methods S800, S900, S1000 and S1100 illustrated in FIGS. 8 to 11 may be divided into two or more sub-blocks, or may be omitted in some embodiments. In addition, although the blocks of the control methods S800, S900, S1000 and S1100 illustrated in FIGS. 8 to 11 are illustrated in sequence, in some cases, some of the blocks may be performed in parallel, or the sequence of any two blocks may be reversed. In addition, the control methods S800, S900, S1000 and S1100 illustrated in FIGS. 8 to 11 may include new blocks associated with functions or operations not illustrated in FIGS. 8 to 11.

Figure 12A:
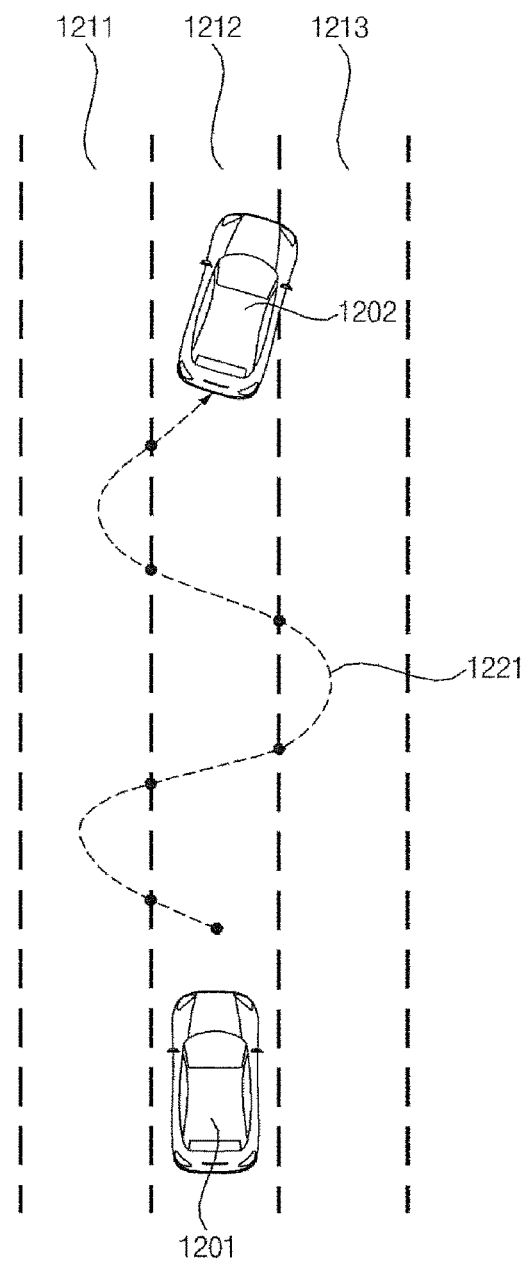
FIGS. 12A to 12C are views respectively illustrating the situation in which the driver assistance apparatus according to one embodiment of the present invention judges whether there are any dangerous vehicles in the vicinity of a vehicle.
Figure 12B:
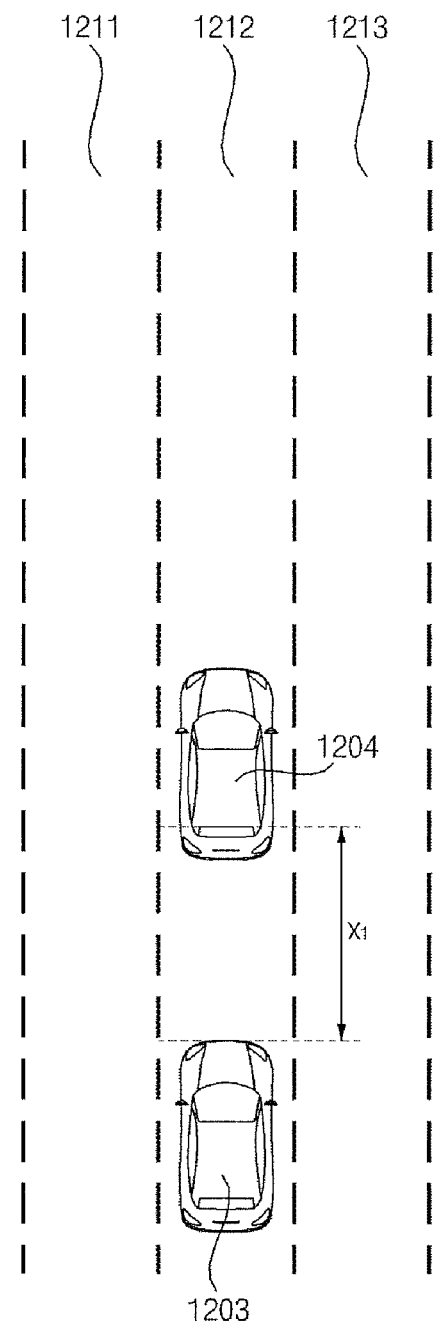
Figure 12C:
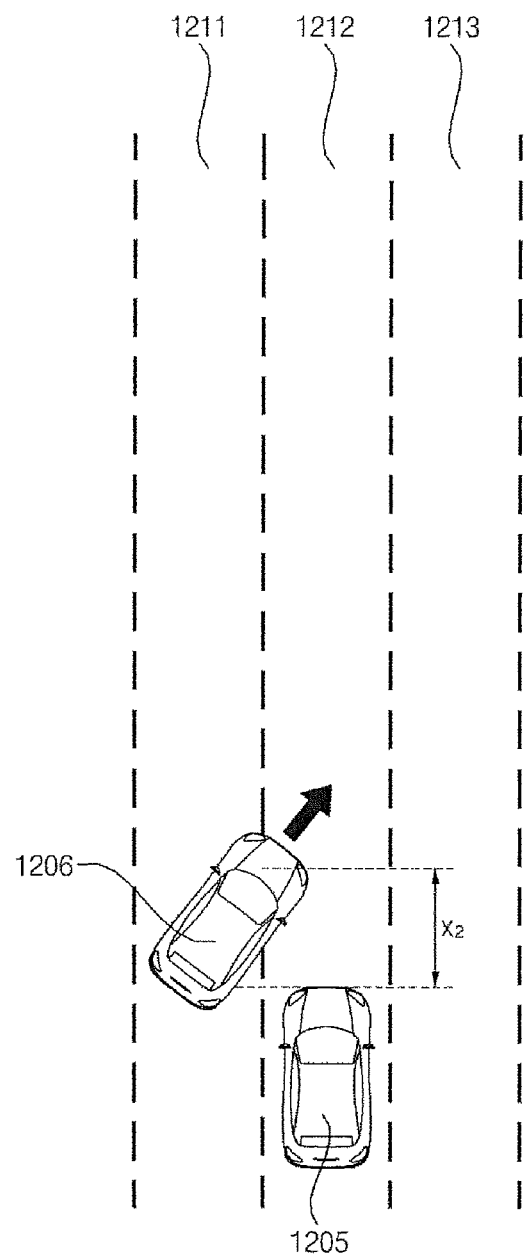

FIGS. 12A to 12C are views respectively illustrating the situation in which the driver assistance apparatus 500 according to one embodiment of the present invention judges whether there are any dangerous vehicles in the vicinity of a vehicle.

FIG. 12A is a top view of a road including a left lane 1211, a center lane 1212, and a right lane 1213. A vehicle 1201 is being driven in the center lane 1212 of the road, and another vehicle 1202 is being driven in front of the vehicle 1201 in the same lane, i.e. the center lane 1212 and in the same direction as the vehicle 1201. For convenience of description, it is assumed that the driver assistance apparatus 500 is included in the vehicle 1201 and the vehicle 1201 corresponds to the vehicle 1 illustrated in FIG. 1.

The sensing unit 160 of the vehicle 1201 may provide the processor 570 with information regarding the movement of the other vehicle 1202. The processor 570 may receive the information regarding the movement of the other vehicle 1202 provided from the sensing unit 160, and may acquire the driving pattern of the other vehicle 1202 based on the received information. The driving pattern of the other vehicle 1202 acquired by the processor 570 may include a driving path 1221 illustrated in FIG. 12A. For example, the driving path 1221 of the other vehicle 1202 may be acquired based on information regarding the movement of the other vehicle 1202 received during the most recent predetermined time period (e.g., 3 seconds) from the current point in time. In addition, the driving pattern of the other vehicle 1202 may be updated, either in real time or periodically.

The processor 570 may compare the driving pattern of the other vehicle 1202 with a first predetermined reference pattern to judge whether the two patterns match each other. Here, the first reference pattern may include a critical value about the number of times that the other vehicle makes a lane change during a prescribed time period (e.g., 3 seconds). When the number of times that the other vehicle 1202 changes lanes during the prescribed time period is equal to or greater than the critical value included in the first reference pattern, the processor 570 may judge that the driving pattern of the other vehicle 1202 matches the first reference pattern. For example, assuming that the critical value included in the first reference pattern is 3 times, the processor 570 may judge that the driving pattern of the other vehicle 1202 matches the first reference pattern because the other vehicle 1202 has the driving pattern of making a lane change a total of 6 times during the prescribed time period. As a result, the processor 570 may judge that the other vehicle 1202 is a dangerous vehicle.

Similar to FIG. 12A, FIG. 12B is a top view of the road including the left lane 1211, the center lane 1212, and the right lane 1213. A vehicle 1203 is being driven in the center lane 1212 of the road, and another vehicle 1204 is being driven in front of the vehicle 1201 in the same lane, i.e. the center lane 1212 and in the same direction as the vehicle 1201. For convenience of description, it is assumed that the driver assistance apparatus 500 is included in the vehicle 1203 and the vehicle 1203 corresponds to the vehicle 1 illustrated in FIG. 1.

The sensing unit 160 of the vehicle 1201 may provide the processor 570 with information regarding the movement of the other vehicle 1204. The processor 570 may receive the information regarding the movement of the other vehicle 1204 provided from the sensing unit 160, and may acquire the driving pattern of the other vehicle 1204 based on the received information. The driving pattern of the other vehicle 1204 acquired by the processor 570 may include the number of times that the other vehicle 1204 has entered a safe distance $x_1$ of the vehicle 1203 during the most recent predetermined time period from the current point in time. Here, the safe distance $x_1$ may be a minimum distance that is set to avoid a collision with an object in front of the vehicle 1203. The safe distance $x_1$ may be set to increase in proportional to the speed of the vehicle.

For example, the driving pattern of the other vehicle 1204 may include the number of times that the other vehicle 1204 has entered the safe distance $x_1$ of the vehicle 1203 during the most recent predetermined time period (e.g., 3 seconds) from the current point in time. Assuming that the vehicle 1203 is being driven at a constant speed, the number of times that the other vehicle 1204 has entered the safe distance $x_1$ of the vehicle 1203 may be the same as the number of times that the other vehicle 1204 suddenly reduces its speed.

The processor 570 may compare the driving pattern of the other vehicle 1204 with a second predetermined reference pattern to judge whether the two patterns match each other. Here, the second reference pattern may include a critical value about the number of times that the other vehicle 1204 has entered the safe distance $x_1$ of the vehicle 1203 during the most recent predetermined time period (e.g., 3 seconds) from the current point in time. When the number of times that the other vehicle 1204 has entered the safe distance $x_1$ of the vehicle 1203 during the most recent predetermined time period (e.g., 3 seconds) from the current point in time is equal to or greater than the critical value included in the second reference pattern, the processor 570 may judge that the driving pattern of the other vehicle 1204 matches the second reference pattern. For example, when the vehicle 1203 is being driven at a constant speed, the critical value included in the second reference pattern is two times, and the other vehicle 1204 has entered the safe distance $x_1$ of the vehicle 1203 a total of three times by suddenly reducing its speed three or more times during the prescribed time period, the processor 570 may judge that the driving pattern of the other vehicle 1204 matches the second reference pattern. As a result, the processor 570 may judge that the other vehicle 1204 is a dangerous vehicle.

Similar to FIG. 12A, FIG. 12C is a top view of the road including the left lane 1211, the center lane 1212, and the right lane 1213. For convenience of description, it is assumed that the driver assistance apparatus 500 is included in a vehicle 1205 and the vehicle 1205 corresponds to the vehicle 1 illustrated in FIG. 1.

The vehicle 1205 is being driven in the center lane 1212 of the road, and another vehicle 1206 is suddenly making a lane change to move from the left lane 1211 to the center lane 1212.

The sensing unit 160 of the vehicle 1205 provides the processor 570 with information regarding the movement of the other vehicle 1206. The processor 570 may receive the information regarding the movement of the other vehicle 1206 provided from the sensing unit 160, and may acquire the driving pattern of the other vehicle 1206 based on the received information.

The driving pattern of the other vehicle 1206, acquired by the processor 570, may include the number of times that the other vehicle 1206 has cut in front of the vehicle 1205 during the most recent predetermined time period from the current point in time. Here, the expression "cutting in front of the vehicle" may mean behavior in which the other vehicle 1206, which is being driven in a lane different from that of the vehicle 1205, suddenly moves to the front of the vehicle 1205 without securing a safe distance $x_2$ from the vehicle 1205. The safe distance $x_2$ may be set to increase in proportional to the speed of the vehicle, and may be the same as or different from the safe distance $x_1$ illustrated in FIG. 12B.

For example, the driving pattern of the other vehicle 1206 may include the number of times that the other vehicle 1206 has cut in front of the vehicle 1205 during the most recent predetermined time period (e.g., 3 seconds) from the current point in time.

The processor 570 may compare the driving pattern of the other vehicle 1206 with a third predetermined reference pattern to judge whether the two patterns match each other. Here, the third reference pattern may include a critical value about the number of times that the other vehicle 1206 has cut in front of the vehicle 1205 during the prescribed time period (e.g., 3 seconds). When the number of times that the other vehicle 1206 has cut in front of the vehicle 1205 during the prescribed time period is equal to or greater than the critical value included in the third reference pattern, the processor 570 may judge that the driving pattern of the other vehicle 1206 matches the third reference pattern. For example, when the critical value included in the third reference pattern is 1 time, and the other vehicle 1206 has cut in front of the vehicle 1205 once during the prescribed time period, the processor 570 may judge that the driving pattern of the other vehicle 1206 matches the third reference pattern. As a result, the processor 570 may judge that the other vehicle 1206 is a dangerous vehicle.

Figure 13A:
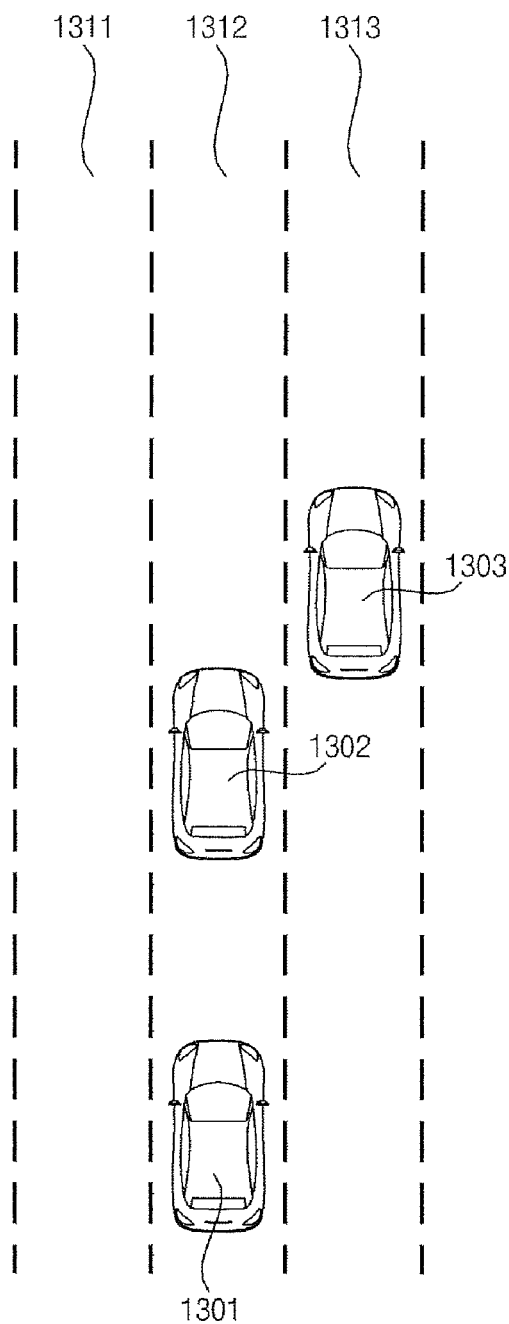
FIGS. 13A and 13B are views illustrating the situation in which the driver assistance apparatus according to one embodiment of the present invention judges whether there are any dangerous vehicles in the vicinity of a vehicle.
Figure 13B:
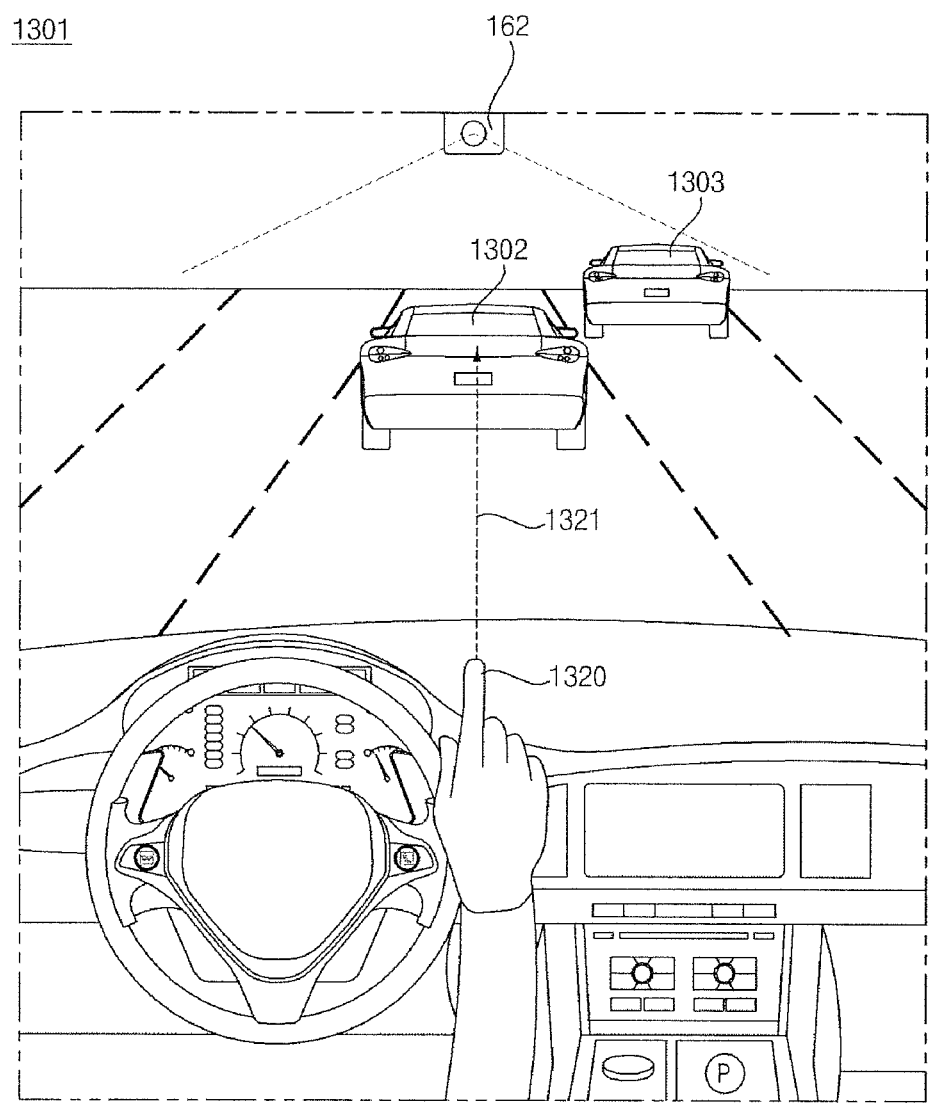

FIGS. 13A and 13B are views illustrating the situation in which the driver assistance apparatus 500 according to one embodiment of the present invention judges whether there are any dangerous vehicles in the vicinity of the vehicle.

FIG. 13A is a top view of a road including a left lane 1311, a center lane 1312, and a right lane 1313. A vehicle 1301 is being driven in the center lane 1312 of the road, a first other vehicle 1302 is being driven in front of the vehicle 1301 in the same lane, i.e. the center lane 1312 and in the same direction as the vehicle 1301, and a second other vehicle 1303 is being driven in the right lane 1313 in the same direction as the vehicle 1301. For convenience of description, it is assumed that the driver assistance apparatus 500 is included in the vehicle 1301 and the vehicle 1301 corresponds to the vehicle 1 illustrated in FIG. 1. In this case, the processor 570 may be tracking the driving pattern of the first other vehicle 1302 and the driving pattern of the second other vehicle 1303 based on information regarding the movement of the first other vehicle 1302 and information regarding the movement of the second other vehicle 1303 provided from the sensing unit 160.

FIG. 13B illustrates an indoor view of the vehicle 1301 in the situation of FIG. 13A. The driver can view the first other vehicle 1302 and the second other vehicle 1303 in front of the vehicle 1301 through the windshield.

The camera 162 may be placed at one side of the interior of the vehicle 1301 (e.g., the ceiling or the dashboard). The camera 162 may be a stereo camera or a depth camera that is capable of acquiring 3D image information regarding the space inside the vehicle 1301. Alternatively, the camera 162 may be an infrared camera. In addition, the camera 162 has a tilt and a view angle to capture an image of at least part of the driver's body (e.g., the head, face, eyes, hands, fingers, upper body, or whole body). As such, the 3D image information acquired by the camera 162 may include the driver's gesture.

Although FIG. 13B illustrates only one camera 162 placed inside the vehicle 1301, a plurality of cameras may be arranged at different positions so as to respectively acquire 3D image information.

The processor 570 may recognize the driver's gesture based on the 3D image information provided from the camera 162. For example, the processor 570 may determine the gesture that the driver is performing at present, selected from among a plurality of predetermined gestures, based on the difference between a previously stored reference image and the acquired 3D image. In another example, when the camera 162 is an infrared camera, the processor 570 may recognize the driver's gesture based on infrared beams that are emitted toward the driver and then reflected by the driver. It should be understood that the scope of the present invention is not limited to the above description, and the driver's gesture may be recognized using other known methods.

FIG. 13B illustrates one example of recognizing the driver's gesture as the processor 570 monitors 3D images including an index finger 1320. The processor 570 may determine the direction in which the finger 1320 of the driver is pointing based on the 3D images, and determine the object at which the finger 1320 is pointing. For example, the processor 570 may calculate a straight line 1321 corresponding to the direction in which the finger 1320 is pointing, and may determine the point on the windshield through which the straight line 1321 passes. For example, the coordinates of the intersection point between the straight line 1321 and the windshield may be acquired. Thereby, the processor 570 may select the first other vehicle 1302, which is viewed at the point where the straight line 1321 meets the windshield, from among the first other vehicle 1302 and the second other vehicle 1303.

The processor 570 may judge that the first other vehicle 1302 selected by the driver's gesture 1320 is a dangerous vehicle. Alternatively, the processor 570 may compare the driving pattern of the first other vehicle 1302 selected by the driver's gesture 1320 with a predetermined reference pattern, and may judge that the first other vehicle 1302 is a dangerous vehicle when the driving pattern of the first other vehicle 1302 matches the predetermined reference pattern.

Figure 14:
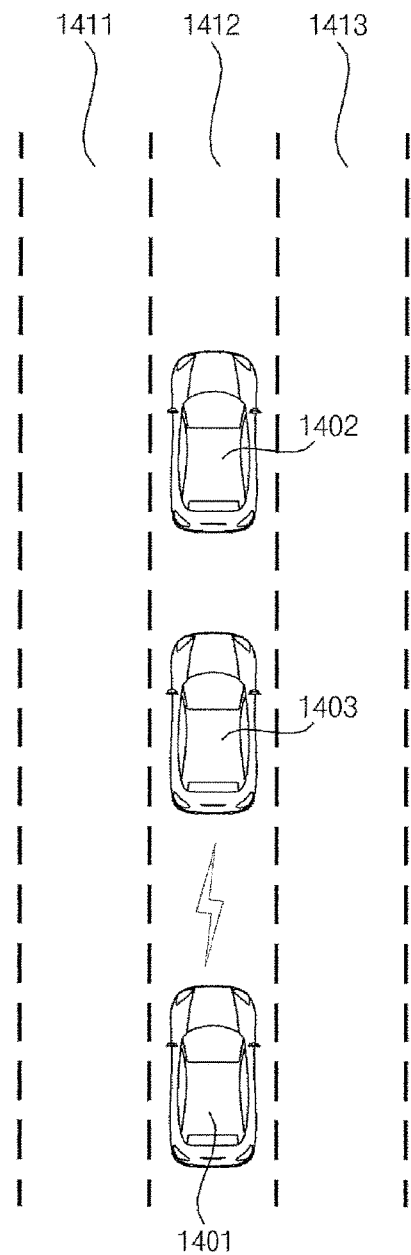
FIG. 14 is a view illustrating the situation in which the driver assistance apparatus according to one embodiment of the present invention determines any dangerous vehicle in the vicinity of a vehicle.

FIG. 14 is a view illustrating the situation in which the driver assistance apparatus 500 according to one embodiment of the present invention judges any dangerous vehicle in the vicinity of the vehicle.

FIG. 14 is a top view of a road including a left lane 1411, a center lane 1412, and a right lane 1413. A first other vehicle 1402 is being driven in front of a second other vehicle 1403, and the second other vehicle 1403 is being driven in front of a vehicle 1401. In addition, all of the three vehicles 1401, 1402, and 1403 are being driven in the center lane 1412 in the same direction. For convenience of description, it is assumed that the driver assistance apparatus 500 is included in the vehicle 1401 and the vehicle 1401 corresponds to the vehicle 1 illustrated in FIG. 1.

In this case, at the position of the vehicle 1401, the first other vehicle 1402 is hidden by the second other vehicle 1403, and therefore the driver of the vehicle 1401 has difficulty in viewing the first other vehicle 1402. When the first other vehicle 1402 is being driven abnormally, there is the risk of an accident because the driver of the vehicle 1401 must inevitably react late.

Meanwhile, the second other vehicle 1403 may acquire information regarding the movement of the first other vehicle 1402 using at least one sensor mounted to the second other vehicle 1403, and thereafter transmit the information regarding the movement of the first other vehicle 1402 to the vehicle 1401. In this case, the vehicle 1401 may receive the information regarding the movement of the first other vehicle 1402 from the second other vehicle 1403 via inter-vehicular communication.

The processor 570 may acquire the driving pattern of the first other vehicle 1402 based on the information regarding the movement of the first other vehicle 1402. Thereafter, the processor 570 may compare the driving pattern of the first other vehicle 1402 with a predetermined reference pattern. When the result of the comparison is that the driving pattern of the first other vehicle 1402 matches the predetermined reference pattern, the processor 570 may judge that the first other vehicle 1402 is a dangerous vehicle. That is, the processor 570 may judge in advance whether the first other vehicle 1402, which is not in the visual field of the driver of the vehicle 1401, is being driven abnormally.

Figure 15A:
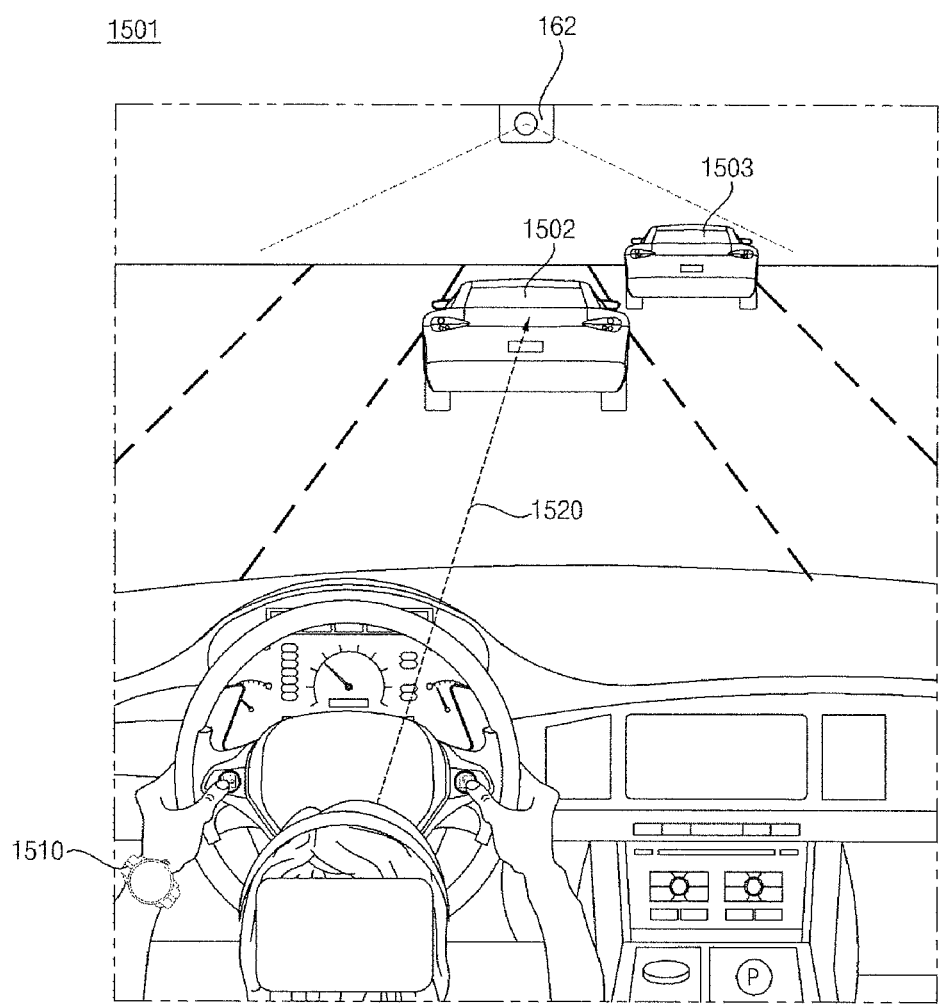
Figure 15B:
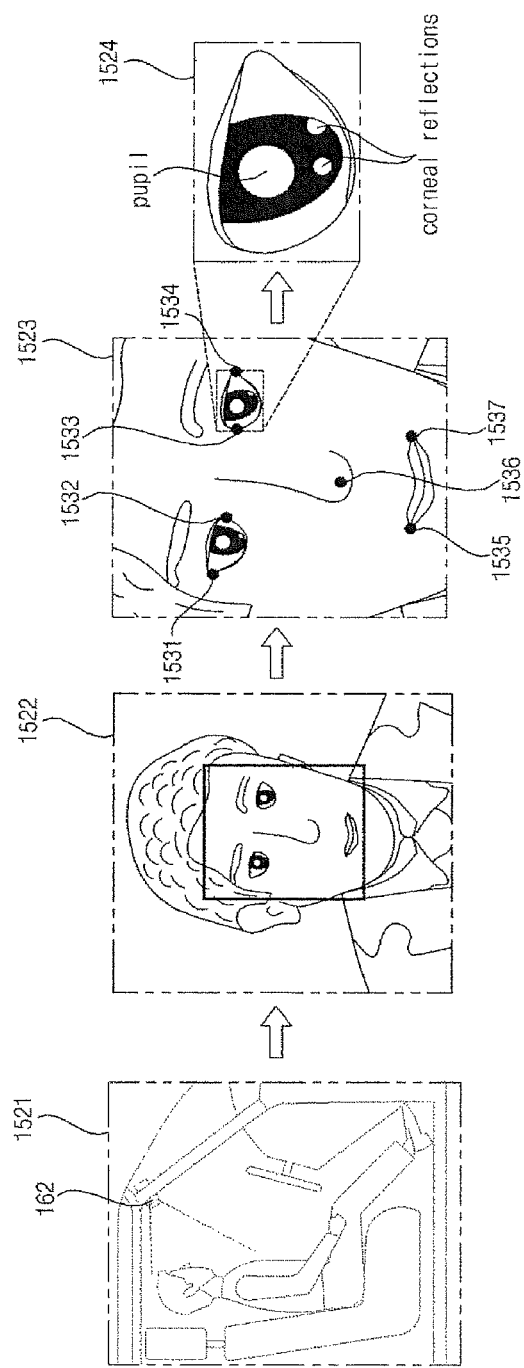

FIGS. 15A to 15C are views respectively illustrating the situation in which the driver assistance apparatus 500 according to one embodiment of the present invention judges any dangerous vehicle in the vicinity of the vehicle.

FIG. 15A illustrates an indoor view of a vehicle 1501 which is being driven behind a first other vehicle 1502 and a second other vehicle 1503. The driver may view the first other vehicle 1502 and the second other vehicle 1503 in front thereof through the windshield.

Similar to FIG. 13B, the camera 162 may be placed at one side inside the vehicle 1501 (e.g., the ceiling or the dashboard). The camera 162 may be a stereo camera or a depth camera that is capable of acquiring 3D image information regarding the space inside the vehicle 1301. Alternatively, the camera 162 may be an infrared camera. In addition, the camera 162 has a tilt and a view angle to capture an image of at least part of the driver's body (e.g., the head, face, eyes, hands, fingers, upper body, or whole body).

Meanwhile, the processor 570 may receive bio-signals of the driver from a wearable device 1510 worn on the driver's body via the communication unit 110. The bio-signals of the driver may include, for example, the heart rate, the amount of sweat, and the body temperature. These bio-signals of the driver may be measured using a variety of sensors included in the wearable device 1510.

FIG. 15B illustrates one example of eye tracking, whereby the driver's gaze 1520 is recognized using the camera 162 illustrated in FIG. 15A. The camera 162 is assumed to be an infrared camera. Referring to FIG. 15B, as illustrated in the first drawing 1521, the processor 570 acquires an image, in which the driver is visible, using the camera 162. At this time, the camera 162 may emit light beams toward the driver's face. Next, as illustrated in the second drawing 1522, the processor 570 detects the driver's face from an image in which the driver is visible. For example, the processor 570 may detect the driver's face by comparing an indoor image provided by the camera 162 with a pre-stored comparative image in order to detect the face of a person from the image in which the driver is visible. Next, as illustrated in the third drawing 1523, the processor 570 detects the driver's eyes by detecting a plurality of facial feature points 1531, 1532, 1533, 1534, 1535, 1536, and 1537 included in the driver's face. The facial feature points 1531, 1532, 1533, 1534, 1535, 1536, and 1537 illustrated in the third drawing 1523 are given by way of example. Next, as illustrated in the fourth drawing 1523, the processor 570 detects the pupil included in the driver's eye and a corneal reflection region. The corneal reflection region is the region in which the light beams emitted from the camera 162 are reflected by the driver's cornea, and may be brighter than other regions. In addition, the processor 570 may calculate the size of the pupils. Thereby, the processor 570 may judge the driver's gaze 1520 illustrated in FIG. 15A by calculating a gaze vector based on the sizes and positions of the pupils and the corneal reflection region.

In this way, the processor 570 may select the first other vehicle 1502, toward which the driver's gaze 1520 is directed, from among the first other vehicle 1502 and the second other vehicle 1503. However, it should be understood that eye tracking is not limited to the process illustrated in FIG. 15B and other known processes may be used.

FIG. 15C is a graph illustrating the relationship between the size of the pupils and the heart rate of the driver and the flow of time. As illustrated, the size of the pupils and the heart rate of the driver may vary over time.

The processor 570 may judge whether the first other vehicle 1502, toward which the driver's gaze 1520 is directed, is a dangerous vehicle based on at least one of the size of the pupils and the heart rate of the driver. For convenience of description, it is assumed that the point in time at which the first other vehicle 1502 is selected is $t_k$.

For example, the processor 570 may judge whether the first other vehicle 1502 is a dangerous vehicle based on variation in the size of the pupils and the heart rate of the driver during a period from before a prescribed time $\Delta t$ to after the prescribed time $\Delta t$ on the basis of the point in time $t_k$ at which the first other vehicle 1502 is selected (i.e. a period from $t_k - \Delta t$ to $t_k + \Delta t$).

Specifically, considering the graph illustrating the size of the pupils, the size of the pupils of the driver is below a first critical value $K_1$ at the point in time $t_k - \Delta t$, and exceeds the first critical value $K_1$ at the point in time $t_k + \Delta t$. In addition, considering the graph illustrating the heart rate, the heart rate of the driver is below a second critical value $K_2$ at the point in time $t_k - \Delta t$, and exceeds the second critical value $K_2$ at the point in time $t_k + \Delta t$. Here, the first critical value $K_1$ and the second critical value $K_2$ are values that are preset to judge whether the driver's state is the anxious state, and may be changed according to the driver's input.

Since the size of the pupils and the heart rate increase as the anxiety of a person increases, rapid variation in the size of the pupils and the heart rate before and after the point in time $t_k$ at which the first other vehicle 1502 is selected as illustrated in FIG. 15C may mean the state in which the driver feels anxiety due to the first other vehicle 1502. Thereby, the processor 570 may judge, based on the driver's gaze 1520, that the selected first other vehicle 1502 is a dangerous vehicle.

On the other hand, unlike the illustration of FIG. 15C, when each of the size of the pupils and the heart rate continuously remains below or above the first critical value $K_1$ or the second critical value $K_2$ during the period from $t_k - \Delta t$ to $t_k + \Delta t$, the processor 570 may judge that the first other vehicle 1502 is not a dangerous vehicle.

Figure 16:
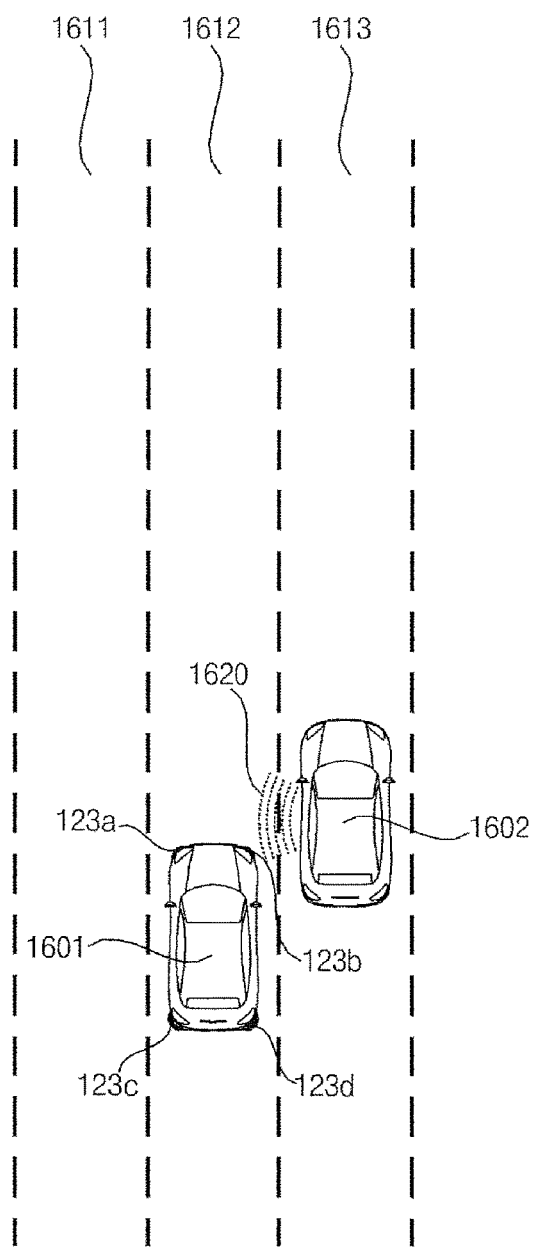
FIG. 16 is a view illustrating the situation in which the driver assistance apparatus according to one embodiment of the present invention determines any dangerous vehicle in the vicinity of a vehicle.

FIG. 16 is a view illustrating the situation in which the driver assistance apparatus 500 according to one embodiment of the present invention judges any dangerous vehicle in the vicinity of the vehicle.

FIG. 16 is a top view of a road including a left lane 1611, a center lane 1612, and a right lane 1613. A vehicle 1601 is being driven in the center lane 1612 and another vehicle 1602 is being driven in the right lane 1613 in the same direction as the vehicle 1601. For convenience of description, it is assumed that the driver assistance apparatus 500 is included in the vehicle 1601 and the vehicle 1601 corresponds to the vehicle 1 illustrated in FIG. 1.

The vehicle 1601 may receive a sound from at least one object which is present in the vicinity of the vehicle 1601 via the microphone 123. For example, a plurality of microphones 123a, 123b, 123c and 123d may be placed at different positions of the vehicle 1601, and at least one of the microphones 123a, 123b, 123c and 123d may receive a sound 1620 discharged from the other vehicle 1602 that is being driven in the vicinity of the vehicle 1601. The sound 1620 discharged from the other vehicle 1602 may be, for example, the voice of a passenger of the other vehicle 1602, exhaust sound of the other vehicle 1602, the horn of the other vehicle 1602, engine noise of the other vehicle 1602, and speaker sound of the other vehicle 1602. In addition, the microphones 123a, 123b, 123c and 123d may convert the received sound 1620 into corresponding electrical signals. The electrical signals may include acoustic information related to the other vehicle 1602.

In addition, the processor 570 may judge the direction and distance of the other vehicle 1602 from the vehicle 1601 based on the strength of sound received by the microphones 123a, 123b, 123c and 123d. For example, when the strength of the sound 1620 received by the microphone 123b is greater than the strength of the same sound 1620 received by the other microphones 123a, 123c and 123d, the processor 570 may judge that the other vehicle 1602 is located near the position at which the microphone 123b is installed.

In addition, the processor 570 may judge whether the other vehicle 1602 is a dangerous vehicle based on the acoustic information included in the electrical signals provided from at least one of the microphones 123*a*, 123*b*, 123*c* and 123*d*. For example, the processor 570 may convert the sound 1620 of the other vehicle 1602 into text via voice recognition, and may judge that the other vehicle 1602 is a dangerous vehicle when characters corresponding to a predetermined profanity (e.g., swear words) are included in the converted text. In another example, the processor 570 may compare the sound 1620 of the other vehicle 1602 with a pre-stored reference sound, and may judge that the other vehicle 1602 is a dangerous vehicle when the sound 1620 of the other vehicle 1602 matches the reference sound. Here, the reference sound is a sound pre-stored in, for example, the memory 540 for judging whether a sound from a surrounding object is a sound associated with a dangerous situation, and may include, for example, a tire puncture sound, a vehicle-to-vehicle collision sound, and the sound of a scream.

Figure 17A:
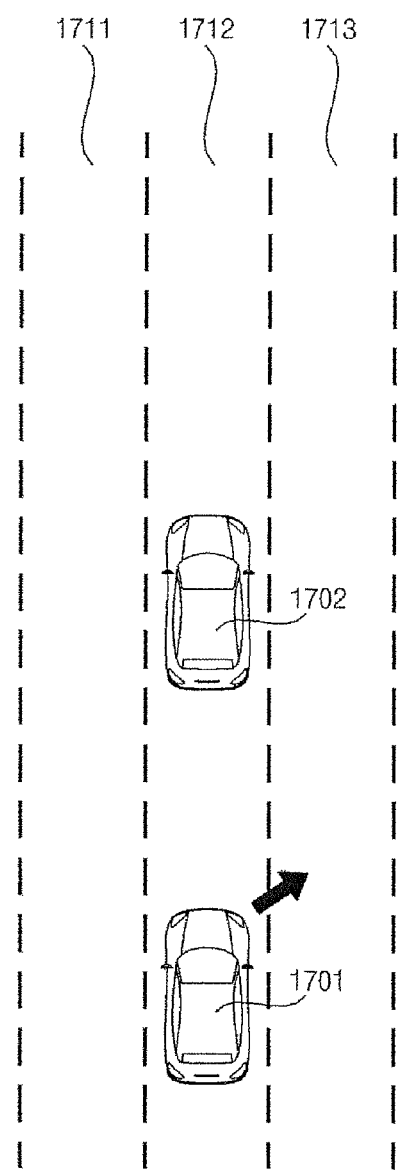
FIGS. 17A and 17B are views illustrating one exemplary operation of the driver assistance apparatus to control the movement of a vehicle according to one embodiment of the present invention.
Figure 17B:
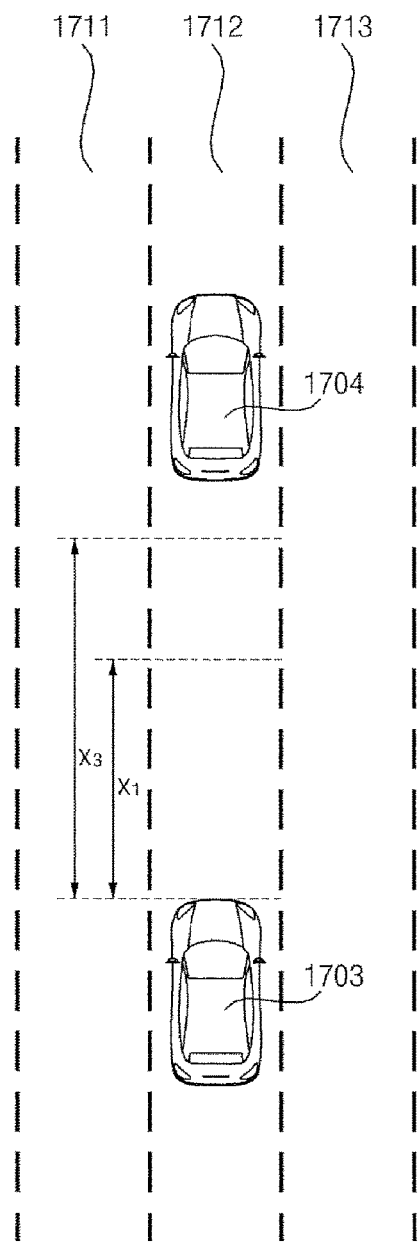

FIGS. 17A and 17B are views illustrating one exemplary operation of the driver assistance apparatus 500 to control the movement of a vehicle according to one embodiment of the present invention.

FIG. 17A is a top view of a road including a left lane 1711, a center lane 1712, and a right lane 1713. A vehicle 1701 is being driven in the center lane 1712 and another vehicle 1702 is being driven in front of the vehicle 1701 in the same center line 1712 and in the same direction as the vehicle 1701. For convenience of description, it is assumed that the driver assistance apparatus 500 is included in the vehicle 1701 and the vehicle 1701 corresponds to the vehicle 1 illustrated in FIG. 1 and that the other vehicle 1702 is a dangerous vehicle that is being driven abnormally. For example, the other vehicle 1702 may be a vehicle that is judged to be a dangerous vehicle by the processor 570 because the other vehicle 1702 changes lanes a number of times beyond a critical value during a prescribed time.

In the situation of FIG. 17A, the processor 570 may operate the vehicle 1701 so as to move to either one of the left lane 1711 and the right lane 1713 from the center lane 1712.

For example, the processor 570 may detect traffic lane markers drawn on the road from a driving image provided from the camera 161, and may judge both boundaries of the right lane 1613 based on the detected traffic lane markers. In addition, the processor 570 may continuously maintain a steering angle required to move from the center lane 1712 to the right lane 1713, and thereafter may provide the steering drive unit 152 with the steering angle. Thereby, the steering drive unit 152 may adjust the heading of the vehicle 1701 by the steering angle so as to move the vehicle 1701 to the right lane 1713 by making a lane change.

Similar to FIG. 17A, FIG. 17B is a top view of the road including the left lane 1711, the center lane 1712, and the right lane 1713. A vehicle 1703 is being driven in the center lane 1712 of the road, and another vehicle 1704 is being driven in front of the vehicle 1703 in the same lane, i.e. the center lane 1712 and in the same direction as the vehicle 1703. For convenience of description, it is assumed that the driver assistance apparatus 500 is included in the vehicle 1703 and the vehicle 1703 corresponds to the vehicle 1 illustrated in FIG. 1 and that the other vehicle 1704 is a dangerous vehicle that is being driven abnormally. For example, the other vehicle 1704 may be a vehicle that is judged to be a dangerous vehicle by the processor 570 because the other vehicle 1704 repeatedly and suddenly reduces its speed and accelerates a number of times exceeding a critical value during a prescribed time period.

In the situation of FIG. 17B, instead of making a lane change, the processor 570 may reduce the speed of the vehicle 1703 to secure a prescribed distance $x_3$ or more between the vehicle 1703 and the other vehicle 1704.

At this time, the prescribed distance $x_3$ may be greater than the safe distance $x_1$ illustrated in FIG. 12B, and may vary according to the driving pattern of the other vehicle 1704. For example, the prescribed distance $x_3$ may be set to 50 m when the number of times that the other vehicle 1704 suddenly reduces its speed during the prescribed time period is 3-5 times, and may increase to 70 m when the number of times that the other vehicle 1704 suddenly reduces its speed during the prescribed time period is 6 or more times.

Meanwhile, FIGS. 17A and 17B illustrate the state in which the vehicle 1701 and the vehicle 1703 have entered the autonomous driving mode. Once having entered the autonomous driving mode, the vehicle 1701 may be driven while automatically performing at least one of the steering, speed reduction, and acceleration thereof based on various signals provided from the sensing unit 160 without any operation on the part of the driver.

Figure 18A:
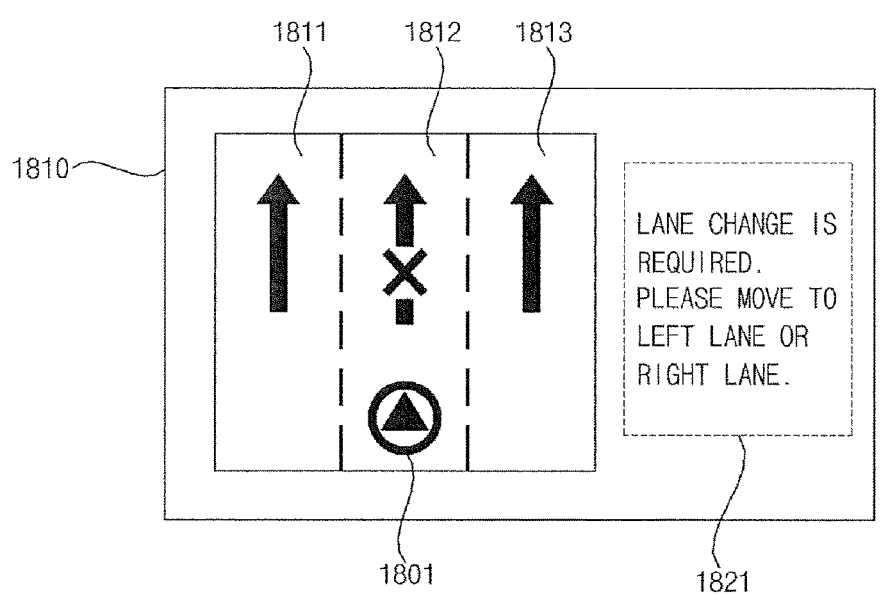
FIG. 18A is a view illustrating one exemplary guide image output to a driver in the situation illustrated in FIG. 17A according to one embodiment of the present invention.

FIG. 18A is a view illustrating one exemplary guide image 1810 output to the driver in the situation illustrated in FIG. 17A according to one embodiment of the present invention. The guide image 1810 may be an image for indicating the behavior that the driver has to perform in order to avoid the dangerous vehicle 1702, and may be displayed on the display unit 580 or the display unit 141 installed inside the vehicle 1701.

As described above, in order to avoid the dangerous vehicle 1702, a lane change operation is required in order to move the vehicle 1701 to either one of the left lane 1711 and the right lane 1713, and the processor 570 may produce the guide image 1810 related thereto.

The guide image 1810 may include three lane images 1811, 1812 and 1813, which respectively indicate the left lane 1711, the center lane 1712, and the right lane 1713. In addition, an indicator 1801 indicating the vehicle 1701 may be displayed in the image 1812 indicating the center lane 1712. In addition, the guide image 1810 may include text 1821 indicating the behavior that the driver has to perform.

The driver of the vehicle 1701 may recognize, via the guide image 1810, that the vehicle 1701 is currently being driven in the center lane 1712 and that it is safe to move to the left lane 1711 or the right lane 1713.

Therefore, the driver of the vehicle 1701 may move the vehicle 1701 to the right lane 1713 by operating the steering wheel as illustrated in FIG. 17A.

Figure 18B:
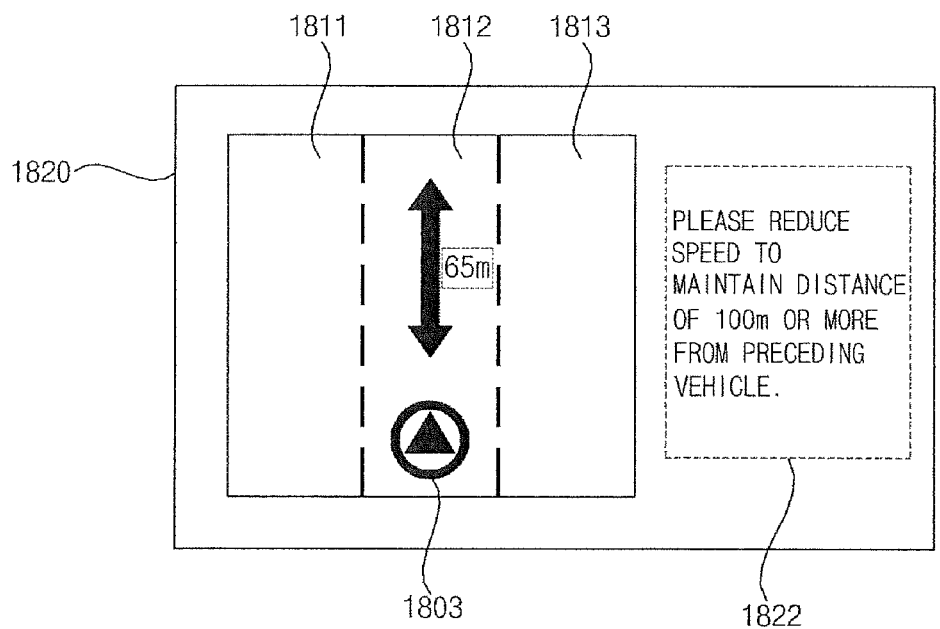
FIG. 18B is a view illustrating another exemplary guide image output to the driver when a dangerous vehicle, illustrated in FIG. 17B, is present according to one embodiment of the present invention.

FIG. 18B is a view illustrating another exemplary guide image 1820 output to the driver when the dangerous vehicle 1704, illustrated in FIG. 17B, is present according to one embodiment of the present invention.

The guide image 1820 may be an image for indicating the behavior that the driver has to perform in order to avoid the dangerous vehicle 1704, and may be displayed on the display unit 580 or the display unit 141 installed inside the vehicle 1703.

As described above, in order to avoid the dangerous vehicle 1704, an operation to reduce the speed of the vehicle 1703 is required in order to secure the prescribed distance $x_3$ from the dangerous vehicle 1704, and the processor 570 may produce the guide image 1820 related thereto.

The guide image 1820 may include the three lane images 1811, 1812 and 1813, which respectively indicate the left lane 1711, the center lane 1712, and the right lane 1713. In addition, an indicator 1803 indicating the vehicle 1703 may be displayed in the image 1812 indicating the center lane 1712. In addition, the guide image 1820 may include text 1822 indicating the behavior that the driver has to perform.

The driver of the vehicle 1703 may recognize, via the guide image 1820, that the vehicle 1703 is currently being driven in the center lane 1712, that the current distance between the vehicle 1703 and the dangerous vehicle 1704 is currently 65 m, and that it is safe to reduce the speed of the vehicle 1703 so as to secure a distance of 100 m or more from the dangerous vehicle 1704.

Therefore, the driver of the vehicle 1703 may operate, for example, a brake pedal so as to reduce the speed of the vehicle 1703 until the distance between the vehicle 1703 and the other vehicle 1704 is equal to or greater than the prescribed distance $x_3$.

Figure 19A:
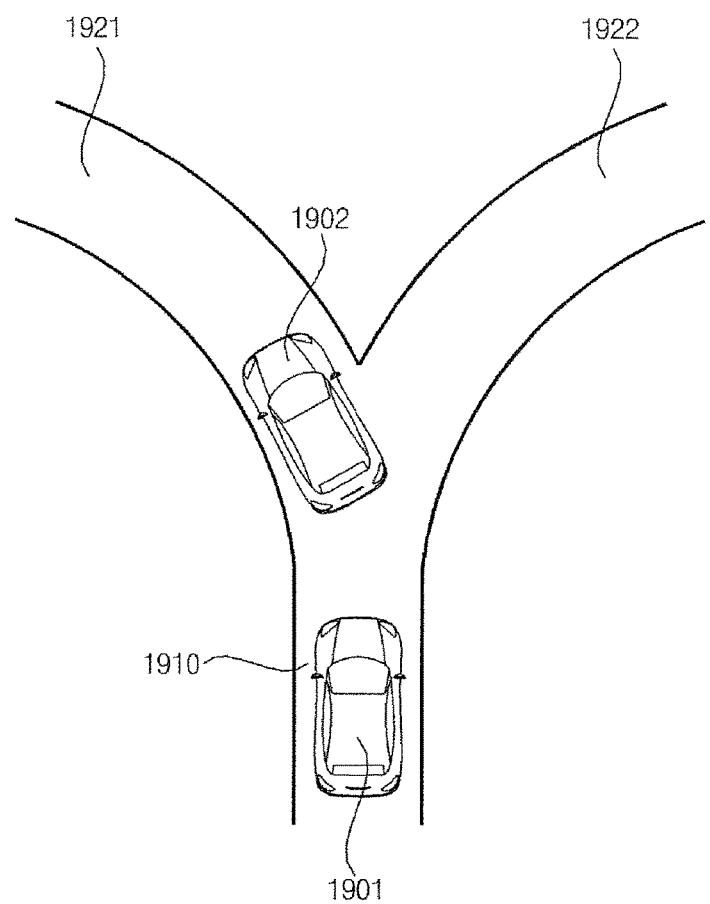
FIG. 19A is a view illustrating the situation in which another vehicle, judged to be a dangerous vehicle, is being driven in the vicinity of a vehicle according to one embodiment of the present invention.

FIG. 19A is a view illustrating the situation in which another vehicle 1902, judged to be a dangerous vehicle, is being driven in the vicinity of a vehicle 1901 according to one embodiment of the present invention.

FIG. 19A is a top view of a road including a main lane 1910, a first branch lane 1921, and a second branch lane 1922. A vehicle 1901 is being driven in the main lane 1910, and the first branch lane 1921 and the second branch lane 1922 are connected to the main lane 1910. For convenience of description, it is assumed that the driver assistance apparatus 500 is included in the vehicle 1901 and the vehicle 1901 corresponds to the vehicle 1 illustrated in FIG. 1.

Referring to FIG. 19A, another vehicle 1902, which is being driven abnormally in front of the vehicle 1901, is heading for the first branch lane 1921 from the main lane 1910. The processor 570 may judge that the other vehicle 1902 is entering the first branch lane 1921 among the first branched lane 1921 and the second branched lane 1922 based on information regarding the movement of the other vehicle 1902 provided from the sensing unit 160.

Figure 19B:
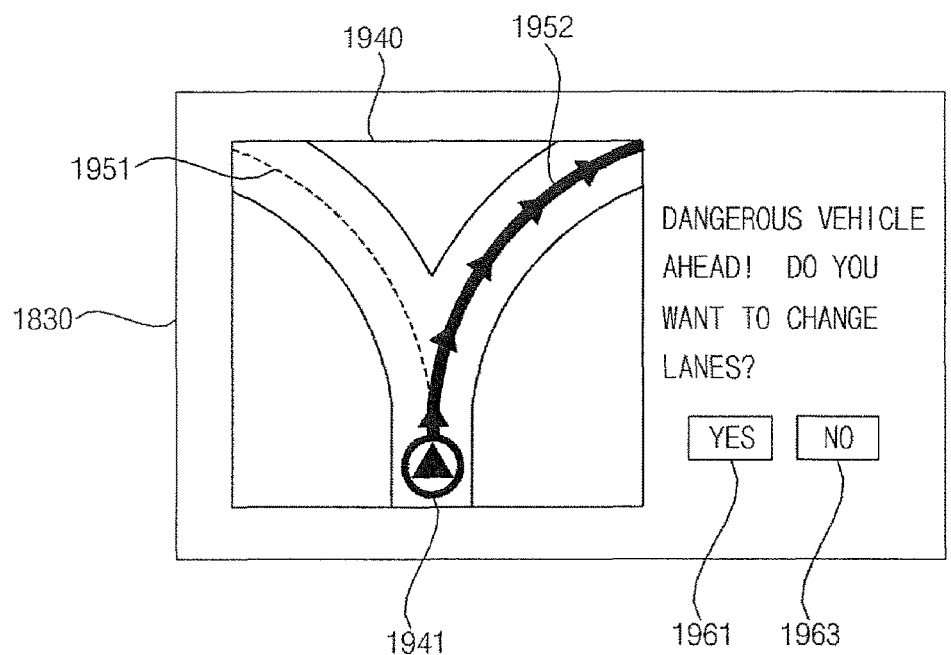
FIG. 19B is a view illustrating one exemplary guide image output to the driver in the situation illustrated in FIG. 19A according to one embodiment of the present invention.

FIG. 19B is a view illustrating one exemplary guide image 1930 output to the driver in the situation illustrated in FIG. 19A according to one embodiment of the present invention. The guide image 1930 is an image for guiding the operation of the vehicle 1901 or the behavior of the driver, which is required in order to avoid the other vehicle 1902, and may be displayed on the display unit 580 or the display unit 141 installed inside the vehicle 1901.

Referring to FIG. 1915, the guide image 1930 may include a route guiding image 1940. In one example, the route guiding image 1940 may include an indicator 1941 indicating the vehicle 1901, an indicator 1951 indicating a currently found route for a previously input destination, and an indicator 1952 indicating a new path to avoid the other vehicle 1902.

In addition, the guide image 1930 may include an icon 1961 to receive user input for approval of the route change, and an icon 1971 to receive user input to refuse the route change. When the driver of the vehicle 1901 selects the icon 1961 via, for example, a touch, the processor 570 may delete the currently found route, and may set a new route indicated by the indicator 1952. When the vehicle 1901 is in the autonomous driving mode, the processor 570 may control at least one of the steering, speed reduction, and acceleration of the vehicle 1901 so as to follow the new path indicated by the indicator 1952.

Figure 20A:
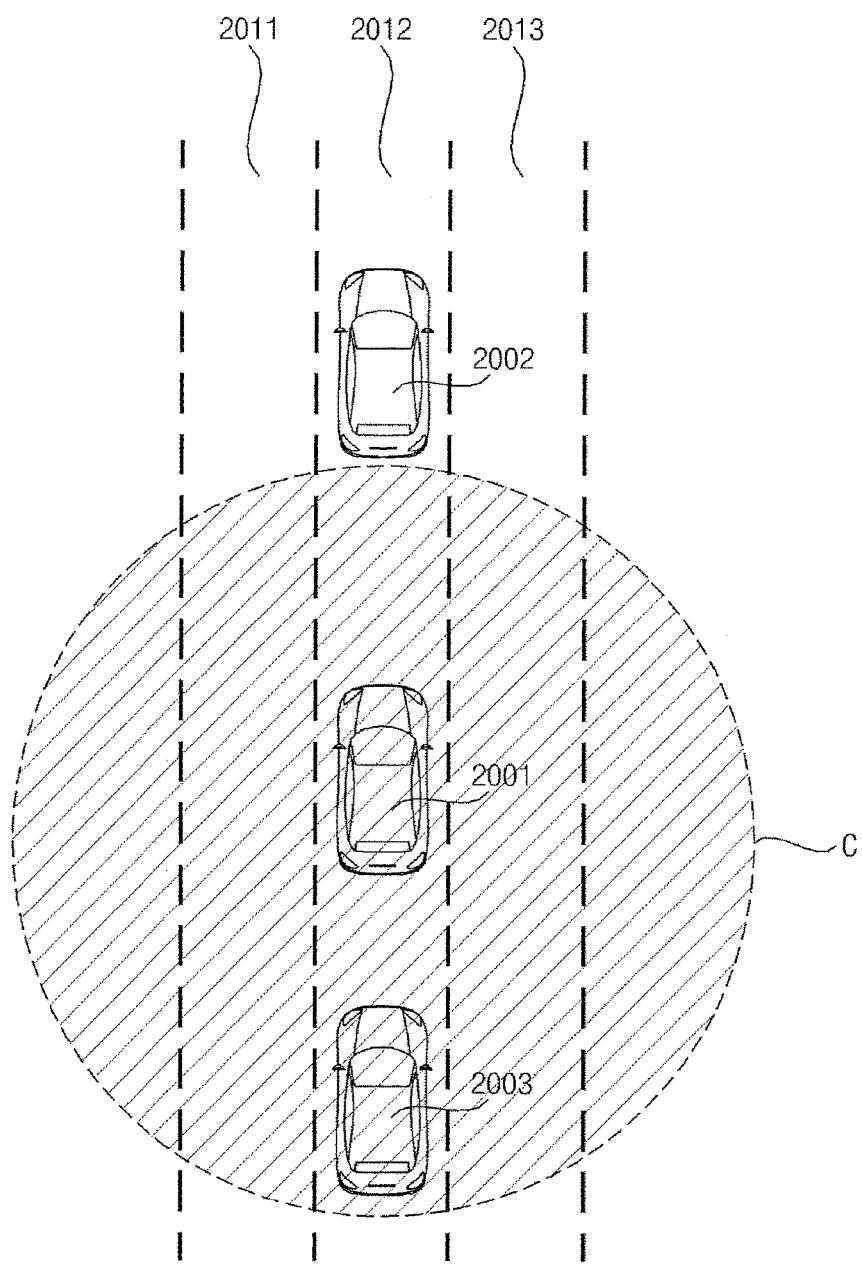
FIG. 20A is a view illustrating the situation in which another vehicle, judged to be a dangerous vehicle, is being driven in the vicinity of a vehicle according to one embodiment of the present invention.

FIG. 20A is a view illustrating the situation in which another vehicle 2002, judged to be a dangerous vehicle, is being driven in the vicinity of a vehicle 2001 according to one embodiment of the present invention.

FIG. 20A is a top view of a road including a left lane 2011, a center lane 2012, and a right lane 2013. All of a vehicle 2001, a first other vehicle 2002, and a second other vehicle 2003 are being driven in the center lane 2012.

For convenience of description, it is assumed that the driver assistance apparatus 500 is included in the vehicle 2001, the vehicle 2001 corresponds to the vehicle 1 illustrated in FIG. 1, and the first other vehicle 2002 is judged to be a dangerous vehicle.

In this case, the vehicle 2001 may outwardly transmit information regarding the movement of the first other vehicle 2002 via inter-vehicular communication. The information regarding the movement of the first other vehicle 2002 is acquired by the sensing unit 160 of the vehicle 2001, and may be transmitted either in real time or periodically to at least one other vehicle located within an inter-vehicular communication possible range C.

The second other vehicle 2003 falls within the inter-vehicular communication possible range C, and may receive the information regarding the movement of the first other vehicle 2002 transmitted from the vehicle 2001. Thereby, the second other vehicle 2003 may recognize and proactively respond to the driving pattern of the first other vehicle 2002, which is hidden by the vehicle 2001 and thus is invisible.

Figure 20B:
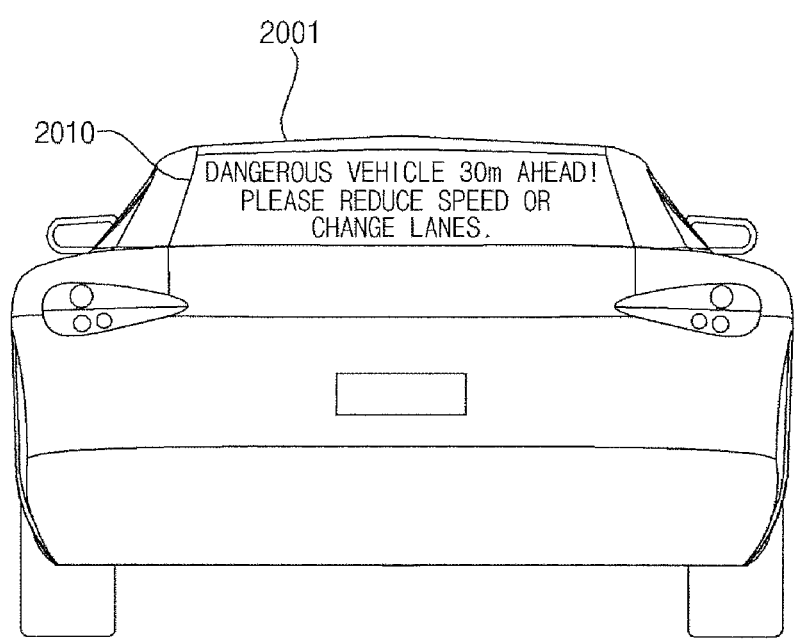
FIG. 20B is a view illustrating the outer appearance of the vehicle according to one embodiment of the present invention in the situation illustrated in FIG. 20A.

FIG. 20B is a view illustrating the outer appearance of the vehicle according to one embodiment of the present invention in the situation illustrated in FIG. 20A.

Referring to FIG. 20B, a display 2010 coupled to the processor 570 may be placed at one side of the vehicle 2001. For example, as illustrated, the display 2010 may be mounted in a region of a rear window of the vehicle 2001. The display 2010 may be included in either one of the display unit 580 illustrated in FIGS. 3A to 3C or the display unit 141 illustrated in FIG. 7.

The processor 570 may produce a guiding message, indicating that the first other vehicle 2002 is being driven in front of the vehicle 2001, so as to notify other vehicles in the vicinity of the vehicle 2001 of the presence of the first other vehicle 2002, and thereafter display the guiding message on the display 2010 as illustrated in FIG. 20B. That is, information regarding the first other vehicle 2002 is displayed on the display 2010 so that it can be checked from the outside.

Thereby, the driver of the second other vehicle 2002, which is being driven behind the vehicle 2001, may be made aware of the presence of the vehicle being driven abnormally in front of the vehicle 2001 by checking the guiding message displayed on the display 2010 even if inter-vehicular communication is impossible.

Figure 21A:
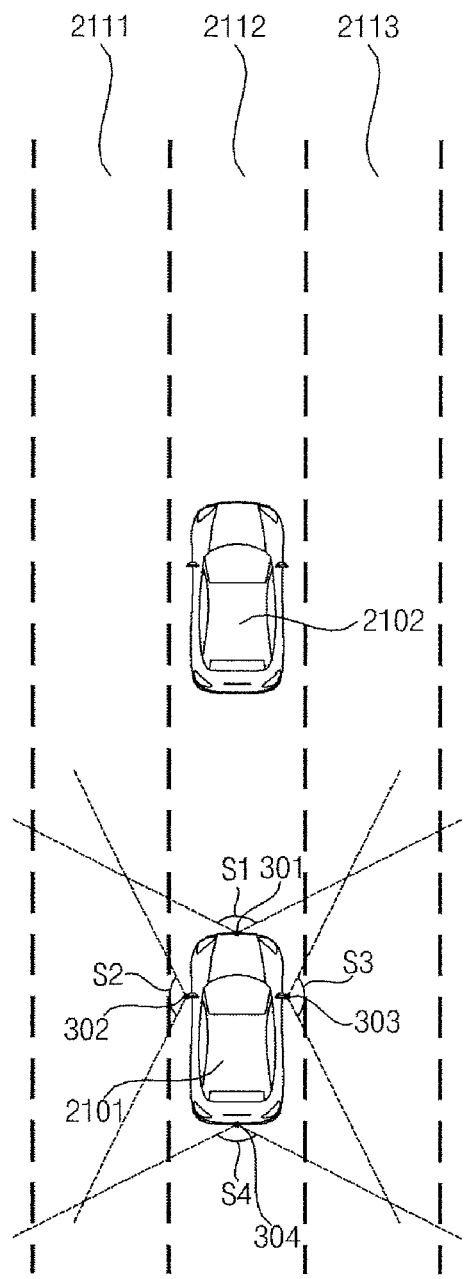
FIGS. 21A to 21C are views illustrating the situation in which another vehicle, judged to be a dangerous vehicle, is being driven in the vicinity of a vehicle according to one embodiment of the present invention.
Figure 21B:
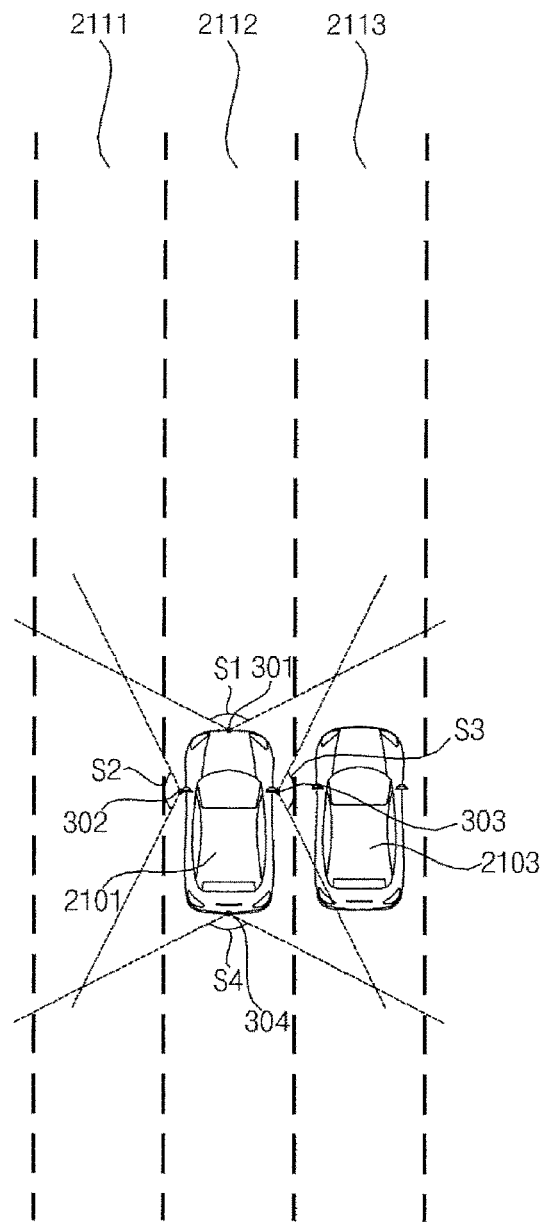
Figure 21C:
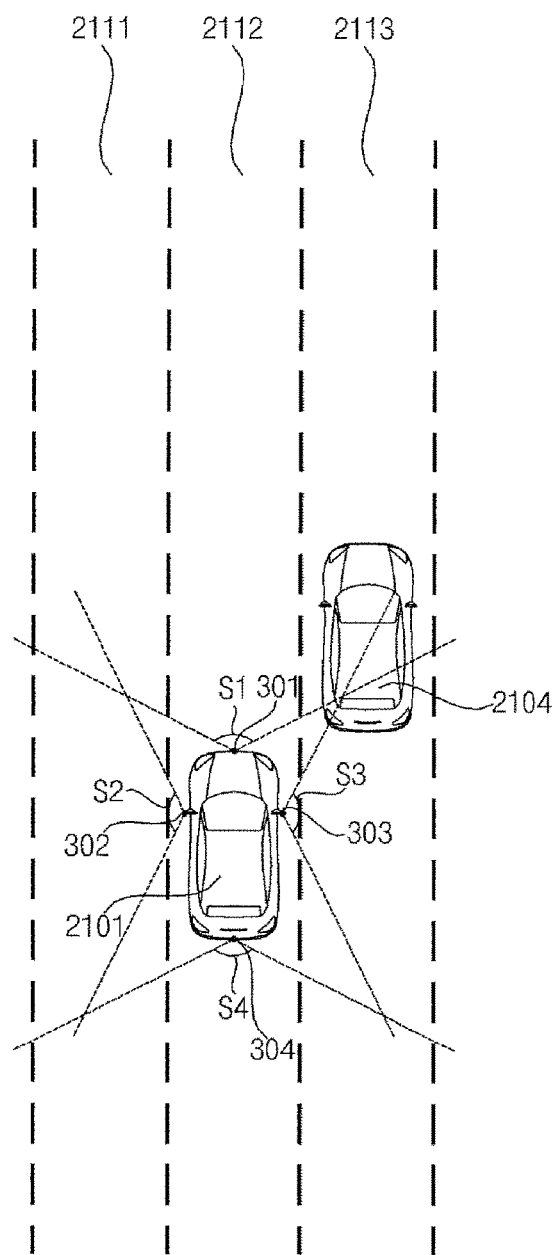

FIGS. 21A to 21C are views illustrating the situation in which other vehicles 2102, 2103 and 2104, judged to be dangerous vehicles, are being driven in the vicinity of a vehicle 2101 according to one embodiment of the present invention. Specifically, FIGS. 21A to 21C are top views of a road including a left lane 2111, a center lane 2112, and a right lane 2113. For convenience of description, it is assumed that the driver assistance apparatus 500 is included in the vehicle 2101, and the vehicle 2101 corresponds to the vehicle 1 illustrated in FIG. 1.

First, referring to FIG. 21A, the other vehicle 2102 is being driven in front of the vehicle 2101, and the processor 570 may judge that the other vehicle 2102 is currently located in front of the vehicle 2101 based on a sensing signal provided from the sensing unit 160.

The vehicle 2101, as illustrated in FIG. 3, may be provided with the cameras 301, 302, 303 and 304. At this time, the camera 301 may have a first view angle S1, the camera 302 may have a second view angle S2, the camera 303 may have a third view angle S3, and the camera 304 may have a fourth view angle S4. Information regarding the arrangement positions and view angles of the respective cameras 301, 302, 303 and 304 may be pre-stored in the processor 570 or the memory 540.

The other vehicle 2102, which is located in front of the vehicle 2101, is included in the view angle S1 of the camera 301, but is not included in the view angles of the other three cameras 302, 303 and 304. In the situation of FIG. 21A, the processor 570 may turn the three cameras 302, 303 and 304 off, and activate only the camera 301. Thereby, the other vehicle 2102 is visible in a driving image formed by the camera 301, and the processor 570 may store the driving image, in which the other vehicle 2102 is visible, from among driving images formed by the camera 301, in a separate storage space defined in the memory 540.

Next, referring to FIG. 21B, unlike FIG. 21A, the other vehicle 2103 is being driven on the right side of the vehicle 2101 and is located parallel to the vehicle 2101, and the processor 570 may judge that the other vehicle 2103 is currently located to the right of the vehicle 2101 based on a sensing signal provided from the sensing unit 160.

In this case, the other vehicle 2103, which is located to the right of the vehicle 2101, is included in the view angle S3 of the camera 303, but is not included in the view angles of the other three cameras 301, 302 and 304. In the situation of FIG. 21B, the processor 570 may turn the three cameras 301, 302 and 304 off, and activate only the camera 303. Thereby, the other vehicle 2103 is visible in a driving image formed by the camera 303, and the processor 570 may store the driving image, in which the other vehicle 2103 is visible, from among driving images formed by the camera 303, in a separate storage space defined in the memory 540.

Next, referring to FIG. 21C, the other vehicle 2104 is being driven in the right lane 2113, and the processor 570 may judge that the other vehicle 2104 is currently located at the right front side of the vehicle 2101 based on a sensing signal provided from the sensing unit 160.

In this case, the other vehicle 2104 is included in the view angle S1 of the camera 301 and the view angle S3 of the camera 303, but is not included in the view angles of the other two cameras 302 and 304. In the situation of FIG. 21C, the processor 570 may turn the two cameras 302 and 304 off and activate only the other two cameras 301 and 303. Thereby, the other vehicle 2104 is visible in driving images formed by the two cameras 301 and 303, and the processor 570 may store the driving images, in which the other vehicle 2104 is visible, from among driving images formed by the two cameras 301 and 303, in a separate storage space defined in the memory 540.

As exemplarily illustrated in FIGS. 21A to 21C, the processor 570 may selectively activate only the camera that is capable of capturing images of other vehicles that are judged to be dangerous vehicles, from among the cameras, which enables the efficient use of the storage space required to record the driving images.

Figure 22:
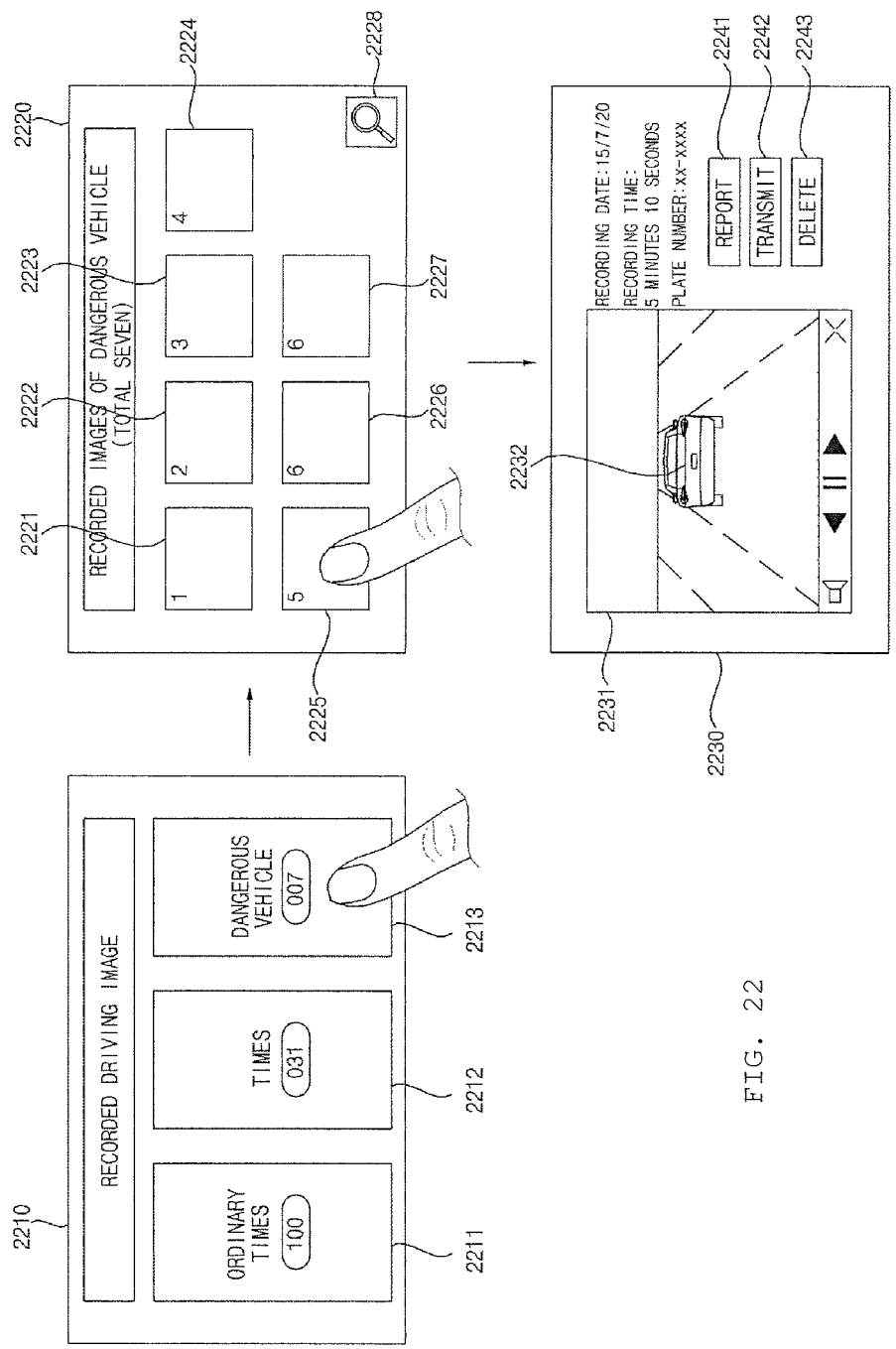
FIG. 22 is a view illustrating one example of a series of user interfaces provided to the driver according to one embodiment of the present invention.

FIG. 22 is a view illustrating one example of a series of user interfaces provided to the driver according to one embodiment of the present invention. The series of user interfaces 2210, 2220 and 2230 illustrated in FIG. 22 may be produced in the form of images by the processor 570 to assist a user in searching for or playing back a specific driving image among recorded driving images, and thereafter be displayed on the display unit 580 or the display unit 141 installed inside the vehicle 1901.

The user interface 2210 includes categories 2211, 2212 and 2213 of images, which are acquired by at least one of a plurality of cameras 195, 196, 197 and 198 illustrated in FIGS. 21A to 21C, and thereafter are recorded in the memory 540. For example, when the category 2211 is selected, a list of 100 images captured during general driving may be provided. When the category 2212 is selected, a list of 31 images captured during parking may be provided. When the category 2213 is selected, a list of 7 images in which a dangerous vehicle is visible may be provided.

When the category 2213 of the user interface 2210 is selected, the processor 570 may display the user interface 2220 including 7 icons 2221, 2222, 2223, 2224, 2225, 2226, and 2227, which correspond to the 7 images in which a dangerous vehicle is visible. In addition, the user interface 2220 may include a search icon 2228. The driver may select the search icon 2228, and thereafter input information related to the image that the user wants to find, so as to search for a specific image.

When any one icon 2225 of the user interface 2220 is selected, the processor 570 may provide the user interface 2230. The user interface 2230 may include a playback window 2231 in which a playback screen of an image related to the icon 2225 is displayed, and a plurality of icons 2232, 2233, and 2234. In addition, various pieces of information related to the image displayed in the playback window 2231 may be displayed in a region of the user interface 2230. For example, the recording date and the recording time of the corresponding image and the license plate number of the dangerous vehicle 2232 may be displayed.

In addition, the driver may select the icon 2241 to report the dangerous vehicle 2232 to the police. In addition, the driver may select the icon 2242 to transmit an image, which is being played back in the user interface 2230, to a pre-registered portable terminal. In addition, the driver may select the icon 2243 to permanently delete the image, which is being played back in the user interface 2230, from the memory 540.

As is apparent from the above description, the effects of a driver assistance apparatus and an operating method for the same according to the present invention are as follows.

Through at least one of the embodiments of the present invention, as a result of judging, based on the movement of at least one another vehicle in the vicinity of a vehicle, whether the other vehicle is a dangerous vehicle, and providing a driver with a notification related to the result of the judgment, it is possible to reduce the anxiety of the driver and to assist the driver in appropriately operating the vehicle.

In addition, through at least one of the embodiments of the present invention, as a result of automatically controlling at least one of the steering, deceleration, and acceleration of a vehicle, which drives in an autonomous driving mode, based on the driving pattern of another vehicle, which is being driven dangerously, it is possible to prevent a collision with the other vehicle.

In addition, through at least one of the embodiments of the present invention, as a result of externally providing information related to another vehicle that is being driven dangerously, it is possible to increase the safety of others.

Effects of the present invention should not be limited to the aforementioned effects and other not-mentioned effects will be clearly understood by those skilled in the art from the claims.

The embodiments of the present invention as described above are not limited to be implemented only via the apparatus and the method and may be implemented via a program that realizes a function corresponding to the configuration of each embodiment of the present invention or a recording medium in which the program is recorded. This implementation will be easily realized by experts in the art of the present invention from the above description of the embodiments.

In addition, it should be readily understood that the invention is not limited to the embodiments described above and the accompanying drawings. Rather, the invention can be modified to incorporate any number of variations, alterations, substitutions, or equivalent arrangements not heretofore described, but which are commensurate with the spirit and scope of the invention. Accordingly, the invention is not to be seen as limited by the foregoing description of the embodiments and the accompanying drawings, and some or all of the embodiments may be selectively combined with one another to achieve various alterations.

What is claimed is:

1. A driver assistance apparatus comprising:
   a sensing unit configured to acquire information regarding an object outside a vehicle, wherein the object includes a first other vehicle being driven in the vicinity of the vehicle;
   a processor configured to:
      judge whether the first other vehicle is a dangerous vehicle based on at least one of the information regarding the object, user input provided from a driver of the vehicle, a state of the driver, or information regarding the first other vehicle provided from a second other vehicle being driven in the vicinity of the vehicle,
      execute at least one predetermined operation based on judging that the first other vehicle is a dangerous vehicle,
      process a plurality of driving images provided from at least one camera of the vehicle into a first driving image that includes the first other vehicle and a second driving image that does not include the first other vehicle, and
      separately store the first driving image and the second driving image; and
   a memory that includes a folder configured to separately store the first driving image from the second driving image.

2. The driver assistance apparatus according to claim 1, wherein the user input is a gesture of the driver, and
   wherein the processor is configured to judge whether the first other vehicle is a dangerous vehicle based on the gesture of the driver pointing to the first other vehicle.

3. The driver assistance apparatus according to claim 1, wherein the processor is configured to acquire a driving pattern of the first other vehicle based on movement of the first other vehicle included in the information regarding the object, to compare the driving pattern of the first other vehicle with a predetermined reference pattern, and to judge whether the first other vehicle is a dangerous vehicle based on determining that the driving pattern of the first other vehicle matching the reference pattern.

4. The driver assistance apparatus according to claim 1, wherein the processor is configured to judge whether the first other vehicle is a dangerous vehicle based on a sound of the first other vehicle that is included in the information regarding the object.

5. The driver assistance apparatus according to claim 1, wherein the predetermined operation includes a first operation, and
   wherein the first operation is an operation of notifying the driver of information regarding the first other vehicle that is judged to be a dangerous vehicle.

6. The driver assistance apparatus according to claim 1, wherein the processor is configured to, based on a plurality of cameras being provided at the vehicle, activate one or more of the cameras that is selected to capture an image of the first other vehicle based on a position of the first other vehicle relative to the vehicle.

7. The driver assistance apparatus according to claim 1, wherein the processor is further configured to:
   receive information regarding the first other vehicle from a second other vehicle being driven in the vicinity of the vehicle via inter-vehicular communication; and
   judge whether the first other vehicle is a dangerous vehicle based on information regarding the first other vehicle provided from the second other vehicle being driven in the vicinity of the vehicle.

8. The driver assistance apparatus according to claim 1, wherein the processor is configured to detect a gaze and pupils of the driver based on an image of the driver that is included in an indoor image of the vehicle, and to judge the state of the driver based on a size of the pupils of the driver when the driver's gaze is directed to the first other vehicle.

9. The driver assistance apparatus according to claim 8, wherein the processor is configured to receive a heart rate of the driver that is acquired by a wearable device worn on the driver, and to judge the state of the driver based on the received heart rate.

10. The driver assistance apparatus according to claim 8, wherein the processor is configured to judge whether the first other vehicle is a dangerous vehicle based on determining that the state of the driver is an anxious state.

11. The driver assistance apparatus according to claim 9, wherein the processor is configured to judge whether the first other vehicle is a dangerous vehicle based on determining that the state of the driver is an anxious state.

12. The driver assistance apparatus according to claim 1, wherein the predetermined operation includes a second operation, and
    wherein the second operation is an operation of predicting a behavior of the first other vehicle based on the driving pattern of the first other vehicle being judged to be a dangerous vehicle.

13. The driver assistance apparatus according to claim 12, wherein the predetermined operation includes a third operation, and
    wherein the third operation is an operation of changing the driving state of the vehicle based on the predicted behavior of the first other vehicle.

14. The driver assistance apparatus according to claim 13, wherein the processor is configured to change the driving state of the vehicle by executing at least one of steering control, acceleration control, or a speed reduction control.

15. The driver assistance apparatus according to claim 1, wherein the predetermined operation includes a fourth operation, and
    wherein the fourth operation is an operation of providing a third other vehicle being driven in the vicinity of the vehicle with information regarding the first other vehicle that is judged to be a dangerous vehicle.

16. The driver assistance apparatus according to claim 15, wherein the processor is configured to transmit the information regarding the first other vehicle to the third other vehicle being driven in the vicinity of the vehicle via inter-vehicular communication.

17. The driver assistance apparatus according to claim 15, wherein the processor is configured to display the information regarding the first other vehicle on a display mounted to an exterior of the vehicle.

18. A driver assistance apparatus comprising:
- a sensing unit configured to acquire information regarding an object outside a vehicle, wherein the object includes a first other vehicle being driven in the vicinity of the vehicle;
- a processor configured to:
  - judge whether the first other vehicle is a dangerous vehicle based on at least one of the information regarding the object, user input provided from a driver of the vehicle, a state of the driver, or information regarding the first other vehicle provided from a second other vehicle being driven in the vicinity of the vehicle,
  - execute at least one predetermined operation based on judging that the first other vehicle is a dangerous vehicle,
  - detect a gaze and pupils of the driver based on an image of the driver that is included in an indoor image of the vehicle, and
  - judge the state of the driver based on a size of the pupils of the driver when the driver's gaze is directed to the first other vehicle,
  - process a plurality of driving images provided from at least one camera of the vehicle into a first driving image that includes the first other vehicle and a second driving image that does not include the first other vehicle, and
  - separately store the first driving image and the second driving image; and
- a memory that includes a folder configured to separately store the first driving image from the second driving image.

* * * * *